(12) United States Patent
Parkinson

(10) Patent No.: US 11,237,234 B2
(45) Date of Patent: Feb. 1, 2022

(54) MRI MAGNET AND APPARATUS

(71) Applicant: VICTORIA LINK LIMITED, Kelburn (NZ)

(72) Inventor: Benjamin John Parkinson, Belmont (NZ)

(73) Assignee: VICTORIA LINK LIMITED, Wellington (NZ)

( * ) Notice: Subject to any disclaimer, the term of this patent is extended or adjusted under 35 U.S.C. 154(b) by 357 days.

(21) Appl. No.: 16/493,349

(22) PCT Filed: Feb. 13, 2018

(86) PCT No.: PCT/NZ2018/050009
§ 371 (c)(1),
(2) Date: Sep. 12, 2019

(87) PCT Pub. No.: WO2018/174726
PCT Pub. Date: Sep. 27, 2018

(65) Prior Publication Data
US 2020/0064423 A1    Feb. 27, 2020

(30) Foreign Application Priority Data
Mar. 24, 2017   (NZ) ...................................... 730471

(51) Int. Cl.
*G01R 33/381* (2006.01)
*G01R 33/38* (2006.01)
(Continued)

(52) U.S. Cl.
CPC ........ *G01R 33/3802* (2013.01); *A61B 5/0042* (2013.01); *G01R 33/381* (2013.01);
(Continued)

(58) Field of Classification Search
CPC .............. G01R 33/3808; G01R 33/381; G01R 33/3815; G01R 33/385; A61B 5/0042
See application file for complete search history.

(56) References Cited

U.S. PATENT DOCUMENTS 5,045,794 A     9/1991  Dorri et al.
5,382,904 A *   1/1995  Pissanetzky ....... G01R 33/3806
                                                29/602.1
(Continued)

FOREIGN PATENT DOCUMENTS

WO    2005103746 A2    11/2005
WO    2016025996 A1     2/2016
WO    2018071754 A1     4/2018

OTHER PUBLICATIONS

A. Belov et al., "Passive Shimming Of The Superconducting Magnet For Mri," IEEE Transactions On Applied Superconductivity, vol. 5, Issue 2, pp. 679-681—Jun. 1995.
(Continued)

*Primary Examiner* — Ramon M Barrera
(74) *Attorney, Agent, or Firm* — Polsinelli PC

(57) ABSTRACT

A magnet (7) for use in an apparatus (1) for performing magnetic resonance imaging (MRI) of a patient's head is an asymmetric magnet (7) comprising a plurality of coils (45, 46, 47) that are aligned along a cylindrical axis (29) to provide a magnetic field on the cylindrical axis (29). The magnet (7) has a patient end (23) arranged to be positioned adjacent or against a patient's shoulders with the patient's shoulders outside the magnet (7). The magnet has a recess (27) for receipt of the patient's head and extending into the magnet (7) from the patient end (23). The magnet (7) is configured to provide an imaging volume (35) that is positioned along the cylindrical axis (29) of the magnet (7) in the recess (27), and at least a major part of the imaging volume
(Continued)

(35) has a substantially linear non-zero magnetic field gradient along the cylindrical axis (29).

20 Claims, 16 Drawing Sheets

(51) Int. Cl.
*A61B 5/00* (2006.01)
*G01R 33/3815* (2006.01)
*G01R 33/421* (2006.01)
*A61B 5/055* (2006.01)

(52) U.S. Cl.
CPC ..... *G01R 33/3804* (2013.01); *G01R 33/3808* (2013.01); *G01R 33/3815* (2013.01); *G01R 33/421* (2013.01); *A61B 5/055* (2013.01)

(56) References Cited

U.S. PATENT DOCUMENTS

| 5,396,207 | A | 3/1995 | Dorri et al. |
| 5,416,415 | A | 5/1995 | Dorri et al. |
| 5,446,434 | A | 8/1995 | Dorri et al. |
| 5,801,609 | A | 9/1998 | Laskaris et al. |
| 6,140,900 | A | 10/2000 | Crozier et al. |
| 7,375,528 | B2 | 5/2008 | Crozier et al. |
| 2007/0188173 | A1 | 8/2007 | Overweg |
| 2011/0011102 | A1 | 1/2011 | Gao et al. |
| 2013/0271133 | A1 | 10/2013 | Snyder et al. |
| 2014/0218028 | A1 | 8/2014 | Snyder et al. |
| 2015/0226821 | A1 | 8/2015 | Zhang et al. |
| 2015/0348689 | A1 | 12/2015 | Wang et al. |
| 2016/0274207 | A1 | 9/2016 | Kondo et al. |

OTHER PUBLICATIONS

K. Koch et al., "Sample-Specific Diamagnetic And Paramagnetic Passive Shimming," Journal of Magnetic Resonance, vol. 182, Issue 1, pp. 66-74—Sep. 2006.
Y. Lvovsky et al., "Novel technologies and configurations of superconducting magnets for MRI," Superconductor Science and Technology, vol. 26, No. 9, pp. 093001—Jul. 2013.
International Search Report and Written Opinion dated Feb. 8, 2019, for corresponding PCT Application No. PCT/NZ2018/050009.
Tomasi, D. et al.; "Asymmetrical Gradient Coil for Head Imaging"; Magnetic Resonance in Medicine; vol. 48; pp. 707-714.

* cited by examiner

MRI MAGNET AND APPARATUS

CROSS-REFERENCE TO RELATED APPLICATIONS

This application is a national stage application (under 35 U.S.C. § 371) of PCT/NZ2018/050009, filed Feb. 13, 2018, which claims benefit of New Zealand Application No. 730471, filed Mar. 24, 2017, which are incorporated herein by reference in their entireties.

FIELD OF THE INVENTION

This invention relates to a magnet for use in a magnetic resonance imaging (MRI) apparatus, and to an apparatus utilising the magnet.

BACKGROUND

MRI apparatuses for medical applications are typically large and cumbersome devices, sized to receive a substantial part of a patient's body, or even the patient's entire body. Whilst this enables the MRI apparatus to be used for analysis of all parts of the patient's body, a large amount of space and significant financial investment are required for the apparatus.

Many patients feel claustrophobic when they are inside a typical MRI apparatus, because a substantial part of their body is received in the apparatus for an extended period during MRI imaging. This is exacerbated by the apparatus typically having a narrowly dimensioned patient recess. MRI magnet cost and complexity scales with recess diameter; patient comfort is therefore traded against having a cost-effective and relatively simple apparatus. Imaging of the brain can be particularly uncomfortable, since the head must be positioned at the centre of the patient recess, leading to feelings of claustrophobia. A related limitation is that the compact size of the patient recess makes interaction between a medical provider and the patient difficult, with sound (via headphones) and limited hand gestures of the patient typically being the only means of communication and interaction with the patient.

MRI apparatuses that are sized for imaging a specific portion of a patient's body are also known. For example, MRI apparatuses have been designed to receive a patient's head and a major portion of their torso. These devices share many of the disadvantages of the typical MRI apparatuses described above. In order to achieve the required field uniformity, large magnets are required, leading to bulky devices that are difficult to transport. Patients may still experience claustrophobia because their head is received by a narrowly dimensioned recess which they cannot see out of. Interaction between a medical provider and the patient is still difficult. Because the patient's shoulders and a major portion of their torso are received by the apparatus, the ability to communicate with a medical provider via hand gestures is not significantly improved.

MRI apparatuses typically require at least three parts. A strong, homogenous magnet, a three-axis gradient coil and at least one radio frequency (RF) coil.

A typical MRI magnet utilises coils of superconducting material to provide a sufficiently uniform magnetic field to obtain suitable images. When MRI magnets are configured to receive a substantial part of the patient's body, a large magnet or magnets are required. Low temperature superconducting (LTS) material is often used in the coils of the magnets as it is relatively cost effective and a large amount of the material is required to form the large magnet(s). However, LTS material typically requires the use of a liquid helium cryogen bath to obtain the required operating temperature. Such a cryogen bath is difficult to manufacture, difficult to seal, and adds to the bulk and cost of the apparatus. LTS superconductors also require isothermal radiation shielding to minimise the leakage of thermal radiation to superconducting coils. Again, the shielding adds to the cost, complexity, and bulk of the apparatus.

Conventional MRI apparatuses are also typically considered to require very high magnetic field uniformity of less than about 10 ppm field variation over the imaging volume, and often less than about 2 ppm field variation, to obtain satisfactory MRI images. Conventional design practice necessitates the use of a large amount of conductor material to achieve these design targets, particularly if a relatively compact magnet is required.

In a conventional MRI apparatus that utilises pulsed fields, it is typically necessary to apply additional magnetic field gradients in all of the x, y, and z directions, to enable different slices to be imaged. This approach leads to costly and complex gradient systems in the MRI apparatus.

It is an object of at least preferred embodiments of the present invention to provide a magnet for use in an MRI apparatus and/or an MRI apparatus that addresses at least one of the disadvantages outlined above, or that at least provides the public with a useful alternative.

SUMMARY OF THE INVENTION

In accordance with a first aspect of the present invention, there is provided a magnet for use in an apparatus for performing magnetic resonance imaging (MRI) of a patient's head, wherein the magnet is an asymmetric magnet comprising: a plurality of coils that are aligned along a cylindrical axis to provide a magnetic field on the cylindrical axis; a patient end arranged to be positioned adjacent or against a patient's shoulders with the patient's shoulders outside the magnet; and a recess for receipt of the patient's head and extending into the magnet from the patient end, wherein the magnet is configured to provide an imaging volume that is positioned along the cylindrical axis of the magnet in the recess, and wherein at least a major part of the imaging volume has a substantially linear non-zero magnetic field gradient along the cylindrical axis.

As used herein, the term 'asymmetric magnet' means that the magnet is not axisymmetric about a plane that is orthogonal to the cylindrical axis and that is centred at the isocentre of the imaging volume.

In an embodiment, at least about 75% of the imaging volume has a substantially linear magnetic field gradient along the cylindrical axis, optionally at least about 80% of the imaging volume has a substantially linear magnetic field gradient along the cylindrical axis, optionally at least about 85% of the imaging volume has a substantially linear magnetic field gradient along the cylindrical axis, optionally about 86% of the imaging volume has a substantially linear magnetic field gradient along the imaging volume, and optionally substantially the entire imaging volume has a substantially linear magnetic field gradient along the imaging volume.

In an embodiment, the magnetic field generally increases in a direction from the patient end to an opposite end of the magnet, along the cylindrical axis. In an embodiment, the magnetic field generally decreases in a direction from the patient end to an opposite end of the magnet, along the cylindrical axis.

In an embodiment, the imaging volume is positioned closer to the patient end of the magnet than to an opposite end of the magnet, along the cylindrical axis.

In an embodiment, the magnet comprises a plurality of superconducting coils. In an embodiment, the coils are annular coils that surround the recess. In an embodiment, the coils are coaxial with the cylindrical axis.

In an embodiment, the magnet comprises at least three groups of coils, with at least one group of coils positioned at or toward the patient end having a larger transverse outer dimension than at least one group of coils positioned at or toward the opposite end of the magnet. In an embodiment, the magnet comprises a first group of coils positioned at or toward the patient end and having a first relatively large transverse outer dimension, a second group of coils positioned further from the patient end and having a second relatively small transverse outer dimension, and a third group of coils positioned at or toward the opposite end and having a third transverse outer dimension that is smaller than the second transverse outer dimension.

In an embodiment, the first, second, and third groups of coils are arranged to provide a summation of magnetic field from the first, second, and third group of coils and provide a magnetic field in a first sense. In an embodiment, the first, second, and third groups of coils have the same winding direction, e.g. a positive or clockwise winding direction. In an embodiment, the magnet comprises at least one additional group of coils that is arranged to provide a magnetic field in a second sense that is opposite to the first sense. In an embodiment, the at least one additional group of coils has a winding direction opposite to the first, second, and third groups of coils, e.g. a negative or anti-clockwise winding direction. In an alternative embodiment, all coils are wound in the same direction but the at least one additional group of coils is operatively connected to receive current in an opposite sense to the current that is received by the first, second, and third groups of coils. In an embodiment, said at least one additional group of coils consists of one group of coils, and said one group of coils is positioned between the first group of coils and the second group of coils. In an embodiment, said one group of coils has a transverse outer dimension that is smaller than the transverse outer dimension of the first group of coils and the transverse outer dimension of the second group of coils. In alternative embodiments, the at least one additional group of coils comprises at least two groups of coils.

In an embodiment, at least some of the groups of coils comprise double pancake coils. In an embodiment, substantially all of the groups of coils comprise double pancake coils. Additionally, or alternatively, at least some of the groups of coils may comprise layer wound coils.

In an embodiment, the superconducting coils comprise low temperature superconducting (LTS) material. In an embodiment, the coils comprise Niobium-Tin ($Nb_3Sn$) material or Niobium-Titanium (NbTi) material.

In an embodiment, the coils comprise a superconductive material with a critical temperature that is greater than 20 K. In an embodiment, the coils comprise Magnesium Diboride ($MgB_2$) material.

In an embodiment, the coils comprise high temperature superconducting (HTS) material. In an embodiment, the coils comprise rare-earth barium copper oxide (REBCO) material. In an embodiment, the coils comprise Bismuth-Strontium-Calcium-Copper-Oxide (BSCCO) material.

In an embodiment, at least one of the groups of coils consists of one coil. In an embodiment, all of the groups of coils each consist of one coil. In an embodiment, the coil comprises LTS material.

In an embodiment, at least one of the groups of coils consists of a plurality of coils. In an embodiment, all of the groups of coils each consist of a plurality of coils. In an embodiment, the plurality of coils comprises HTS material.

In an embodiment, no isothermal radiation shield is provided between the coils and room temperature surfaces of the magnet.

In an embodiment, the imaging volume comprises relatively low uniformity of more than about 200 ppm and up to about 4000 ppm field variation over the imaging volume. In an embodiment, the imaging volume comprises relatively low uniformity of more than about 500 ppm and up to about 4000 ppm field variation over the imaging volume. In an embodiment, the imaging volume comprises relatively low uniformity of more than about 1000 ppm and up to about 4000 ppm field variation over the imaging volume. In an embodiment, the imaging volume comprises relatively low uniformity of more than about 1000 ppm and up to about 3000 ppm field variation over the imaging volume.

In an embodiment, the imaging volume has a length of about 150 mm and a transverse dimension of about 190 mm.

In an embodiment, the magnet comprises a window to enable a patient to see out of the magnet when their head is positioned in the recess. In an embodiment, the window comprises an opening that extends through a wall of the magnet from the recess to an exterior of the magnet. In an embodiment, the window comprises a transparent material that covers at least part of the opening.

In accordance with a second aspect of the present invention, there is provided a magnet for use in an apparatus for performing magnetic resonance imaging (MRI) of a patient's head, wherein the magnet is an asymmetric magnet comprising a plurality of superconducting coils that are positioned around a cylindrical axis to provide a magnetic field on the cylindrical axis, wherein the magnet comprises: a patient end arranged to be positioned adjacent or against a patient's shoulders with the patient's shoulders outside the magnet; and a recess for receipt of the patient's head extending into the magnet from the patient end, wherein the magnet is configured to provide an offset imaging volume in the recess, wherein the imaging volume has an isocentre that is positioned closer to the patient end of the magnet than to the opposite end of the magnet; and wherein the magnet comprises at least three groups of coils in a generally tapering arrangement, with a first group of coils positioned at or toward the patient end having a larger transverse outer dimension than a transverse outer dimension of a second group of coils positioned further from the patient end, and a third group of coils positioned at or toward an opposite end of the magnet having a transverse outer dimension that is smaller than the transverse outer dimension of the second group of coils.

In an embodiment, the magnet is configured to only receive the patient's head and optionally part of the patient's neck, such that the magnet is configured for use as part of a head-only MRI apparatus. In an embodiment, the magnet is configured to provide an imaging volume that is sized and positioned to overlay a typical adult patient's brain.

In an embodiment, the magnet defines the cylindrical axis, and the recess and the imaging volume are coaxial with the cylindrical axis.

In an embodiment, the isocentre is positioned less than about 170 mm from the patient end of the magnet. In an embodiment, the isocentre is positioned less than about 169 mm from the patient end, optionally less than about 168 mm from the patient end, and optionally at about 167 mm from the patient end. In an embodiment, the isocentre is positioned less than about 167 mm from the patient end. In an embodiment, the isocentre is positioned more than about 120 mm from the patient end, optionally more than about 130 mm from the patient end, optionally more than about 140 mm from the patient end, optionally more than about 150 mm from the patient end, optionally more than about 160 mm from the patient end.

In an embodiment, the isocentre is positioned less than about 165 mm above a patient end of the first group of coils, optionally less than about 160 mm above the patient end of the first group of coils, optionally at about 157 mm above the patient end of the first group of coils, optionally less than about 157 mm above the patient end of the first group of coils, optionally at about 150 mm above the patient end of the first group of coils. In an embodiment, the isocentre is positioned more than about 75 mm above the patient end of the first group of coils.

In an embodiment, the isocentre is positioned less than about 200 mm below a top of the third group of coils, optionally less than about 195 mm below the top of the third group of coils, optionally less than about 190 mm below the top of the third group of coils, optionally at about 189 mm below the top of the third group of coils.

In an embodiment, the magnet has a length from the patient end to the opposite end of less than about 400 mm, optionally less than about 390 mm, optionally less than about 385 mm, optionally less than about 380 mm, optionally less than about 375 mm, optionally about 374 mm. In an embodiment, the magnet has a length from the patient end to the opposite end of more than about 350 mm. In an embodiment, the magnet has a length from the patient end to the opposite end of between about 350 mm and about 400 mm. In an embodiment, the magnet has a length from the patient end to the opposite end of between about 374 mm and about 400 mm.

In an embodiment, the coils are annular coils that surround the recess. In an embodiment, the coils are coaxial with the cylindrical axis.

In an embodiment, the first, second, and third groups of coils are arranged to provide a summation of magnetic field from the first, second, and third group of coils and provide a magnetic field in a first sense. In an embodiment, the first, second, and third groups of coils have the same winding direction, e.g. a positive or clockwise winding direction. In an embodiment, the magnet comprises at least one additional group of coils that is arranged to provide a magnetic field in a second sense that is opposite to the first sense. In an embodiment, the at least one additional group of coils has a winding direction opposite to the first, second, and third groups of coils, e.g. a negative or anti-clockwise winding direction. In an alternative embodiment, all coils are wound in the same direction but the at least one additional group of coils is operatively connected to receive current in an opposite sense to the current that is received by the first, second, and third groups of coils. In an embodiment, said at least one additional group of coils consists of one group of coils, and said one group of coils is positioned between the first group of coils and the second group of coils. In an embodiment, said one group of coils has a transverse outer dimension that is smaller than the transverse outer dimension of the first group of coils and the transverse outer dimension of the second group of coils. In alternative embodiments, the at least one additional group of coils comprises at least two groups of coils.

In an embodiment, at least some of the groups of coils comprise double pancake coils. In an embodiment, substantially all of the groups of coils comprise double pancake coils. Additionally or alternatively, at least some of the groups of coils may comprise layer-wound coils.

In an embodiment, the superconducting coils comprise low temperature superconducting (LTS) material. In an embodiment, the coils comprise Niobium-Tin ($Nb_3Sn$) material or Niobium-Titanium (NbTi) material.

In an embodiment, the coils comprise a superconductive material with a critical temperature that is greater than 20 K. In an embodiment, the coils comprise Magnesium Diboride ($MgB_2$) material.

In an embodiment, the coils comprise high temperature superconducting (HTS) material. In an embodiment, the coils comprise rare-earth barium copper oxide (REBCO) material. In an embodiment, the coils comprise Bismuth-Strontium-Calcium-Copper-Oxide (BSCCO) material.

In an embodiment, at least one of the groups of coils consists of one coil. In an embodiment, all of the groups of coils each consist of one coil. In an embodiment, the coil comprises LTS material.

In an embodiment, at least one of the groups of coils consists of a plurality of coils. In an embodiment, all of the groups of coils each consist of a plurality of coils. In an embodiment, the plurality of coils comprises HTS material.

In an embodiment, no isothermal radiation shield is provided between the coils and room temperature surfaces of the magnet.

In an embodiment, the imaging volume has a substantially ellipsoidal shape.

In an embodiment, the imaging volume comprises relatively low uniformity of more than about 200 ppm and up to about 4000 ppm field variation over the imaging volume. In an embodiment, the imaging volume comprises relatively low uniformity of more than about 500 ppm and up to about 4000 ppm field variation over the imaging volume. In an embodiment, the imaging volume comprises relatively low uniformity of more than about 1000 ppm and up to about 4000 ppm field variation over the imaging volume. In an embodiment, the imaging volume comprises a relatively low uniformity of more than about 1000 ppm and up to about 3000 ppm field variation over the imaging volume. In an embodiment, the imaging volume has a length of about 150 mm and a transverse dimension of about 190 mm.

In an embodiment, the magnet comprises a window to enable a patient to see out of the magnet when their head is positioned in the recess. In an embodiment, the window comprises an opening that extends through a wall of the magnet from the recess to an exterior of the magnet. In an embodiment, the window comprises a transparent material that covers at least part of the opening.

The magnet of the second aspect may have any one or more features outlined above in relation to the first aspect.

In accordance with a third aspect of the present invention, there is provided an MRI apparatus for imaging a patient's head, the MRI apparatus comprising the magnet outlined above in relation to the first or second aspect.

In an embodiment, the MRI apparatus is a head-only MRI apparatus.

The term 'comprising' as used in this specification and claims means 'consisting at least in part of'. When interpreting statements in this specification and claims which include the term 'comprising', other features besides the features prefaced by this term in each statement can also be present. Related terms such as 'comprise' and 'comprised' are to be interpreted in a similar manner.

Any of the above aspects of the invention may include any one or more of the features and/or functionality outlined above or herein in relation to any of the other aspects of the invention. Additionally, any of the above aspects may be provided in suitable combination(s), such as those outlined in relation to other aspects, to provide desired functionality.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

This invention may also be said broadly to consist in the parts, elements and features referred to or indicated in the specification of the application, individually or collectively, and any or all combinations of any two or more said parts, elements or features.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting. Where specific integers are mentioned herein which have known equivalents in the art to which this invention relates, such known equivalents are deemed to be incorporated herein as if individually set forth.

As used herein the term '(s)' following a noun means the plural and/or singular form of that noun.

As used herein the term 'and/or' means 'and' or 'or', or where the context allows both. The invention consists in the foregoing and also envisages constructions of which the following gives examples only.

BRIEF DESCRIPTION OF THE DRAWINGS

The present invention will now be described by way of example only and with reference to the accompanying drawings in which:

FIG. 6(a) is a front view of the magnet, FIG. 6(b) is a top view of the magnet, FIG. 6(c) is a sectioned side view of the magnet, FIG. 6(d) is a sectioned side view showing a patient's head in position in the recess of the magnet, and FIG. 6(e) is a sectioned front view showing a patient's head in position in the recess of the magnet;

DETAILED DESCRIPTION OF PREFERRED EMBODIMENTS

General Description

Figure 1:
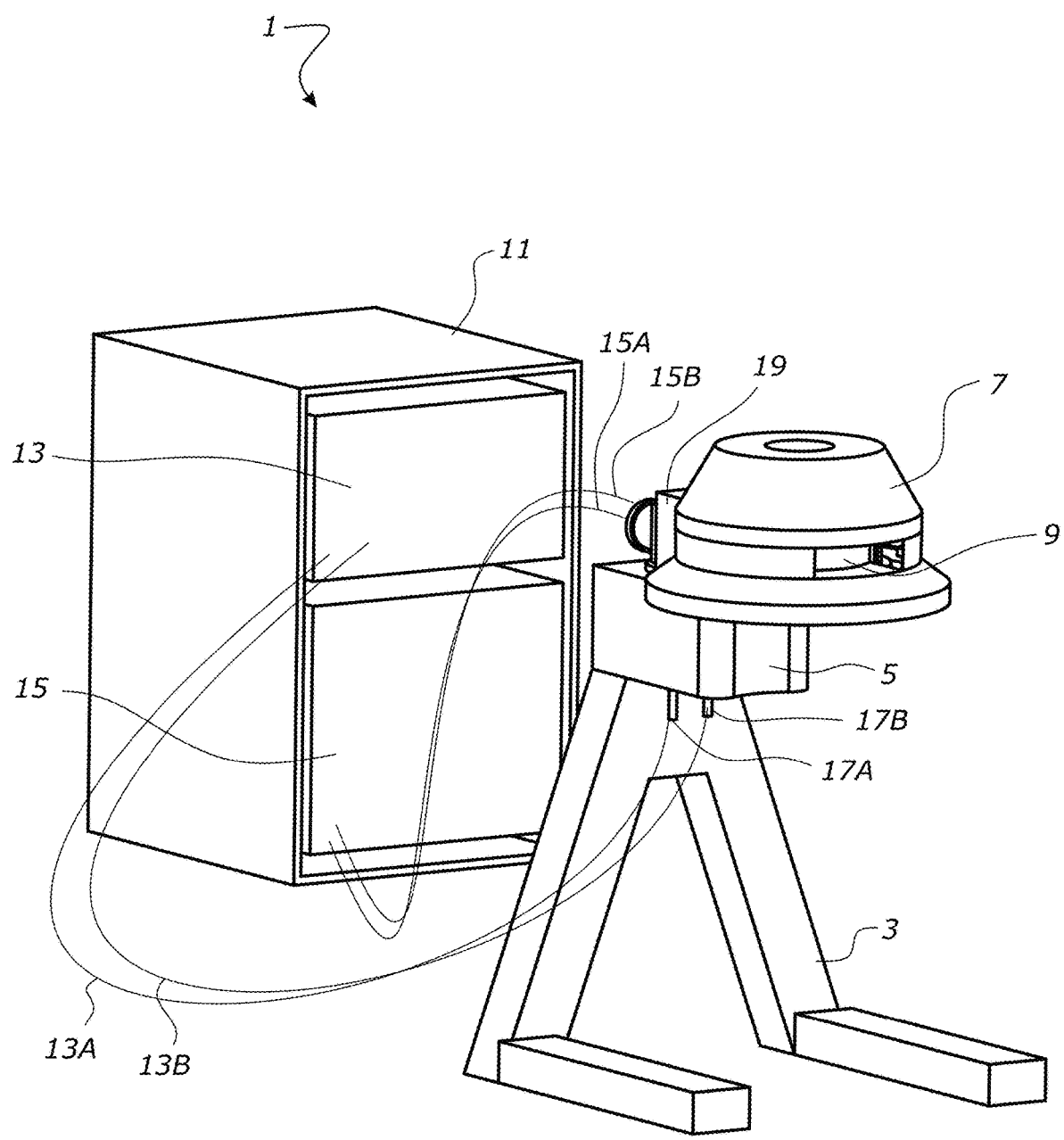
FIG. 1 is a perspective view of a head-only magnetic resonance imaging apparatus in accordance with an embodiment of the present invention.

FIG. 1 shows a schematic drawing of a head-only MRI apparatus 1 for performing magnetic resonance imaging (MRI) of a patient's head. The apparatus 1 comprises a stand 3, a manifold box 5 located at or adjacent the top of the stand 3 and supported by the stand 3, and a magnet 7 connected to the manifold box 5. The magnet has a window 9. An equipment rack 11 is provided which comprises a power supply and controller 13 and a helium compressor 15. The power supply and controller 13 provides current to the magnet 7 via current leads 13A, 13B that are connected to the magnet coils through current injection points 17A, 17B mounted on the manifold box 5. The helium compressor 15 provides compressed helium via helium lines 15A, 15B to the cryocooler 19 which in turn cools the magnet 7.

FIG. 2, FIG. 3, FIG. 4 and FIG. 5 show a perspective view, an exploded perspective view, a front view and a side view respectively of a patient P in position in the apparatus.

Reference herein to a patient is to an averagely sized adult human patient.

Figure 2:
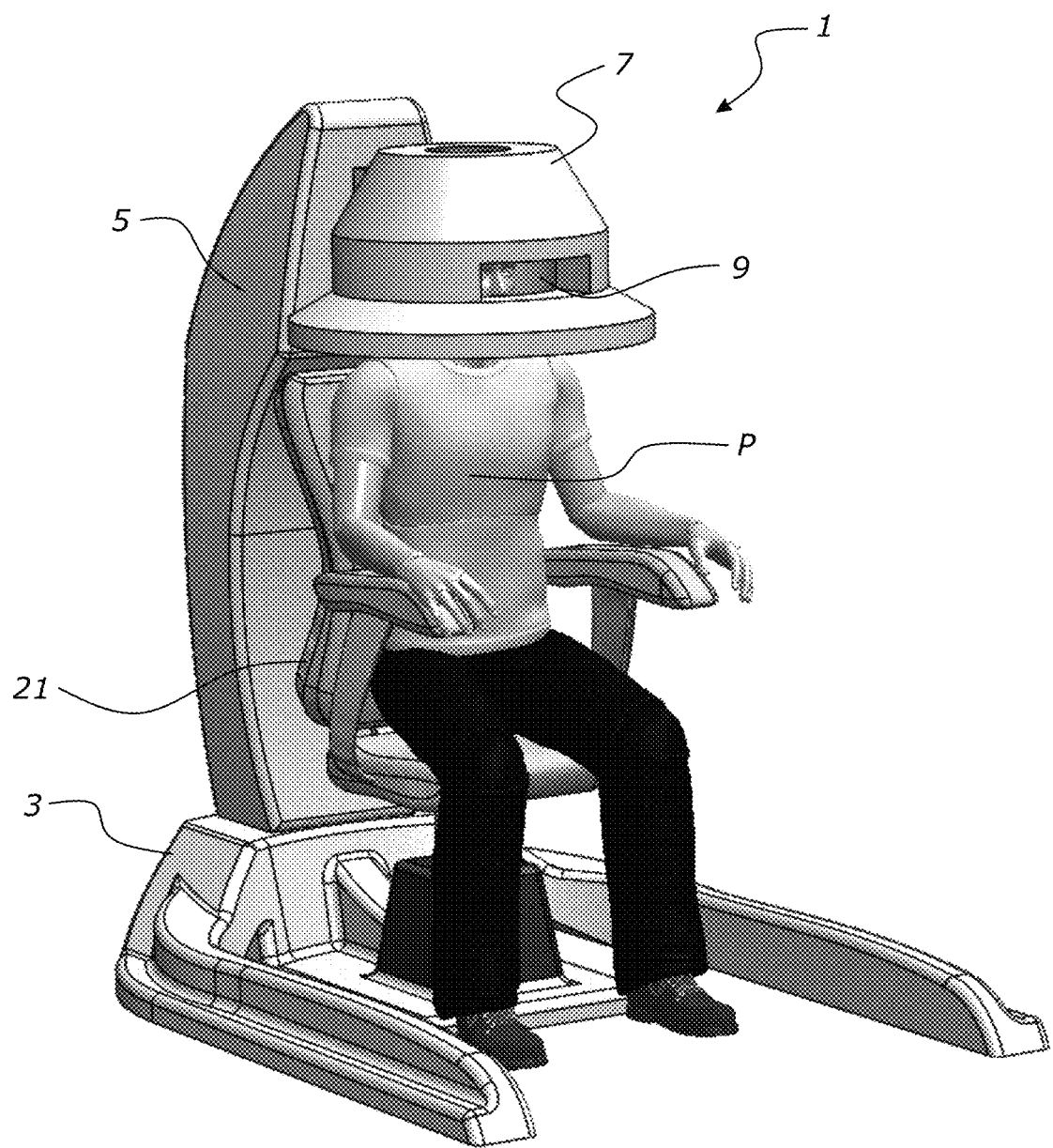
FIG. 2 is a perspective view similar to FIG. 1, but showing a patient in position in the apparatus.

The stand 3 may be configured for use by a patient in a standing position or in a seated position. As shown in FIG. 2, the stand 3 may have a seat 21 for supporting the patient P in a seated configuration. The seat 21 may be height adjustable.

It can be seen from FIG. 2 that in use of the apparatus 1, the patient's head is positioned in the magnet 7 with their eyes aligned with a window 9 of the magnet 7 so the patient can see outside the magnet and respond to visual cues outside the magnet 7.

Figure 3:
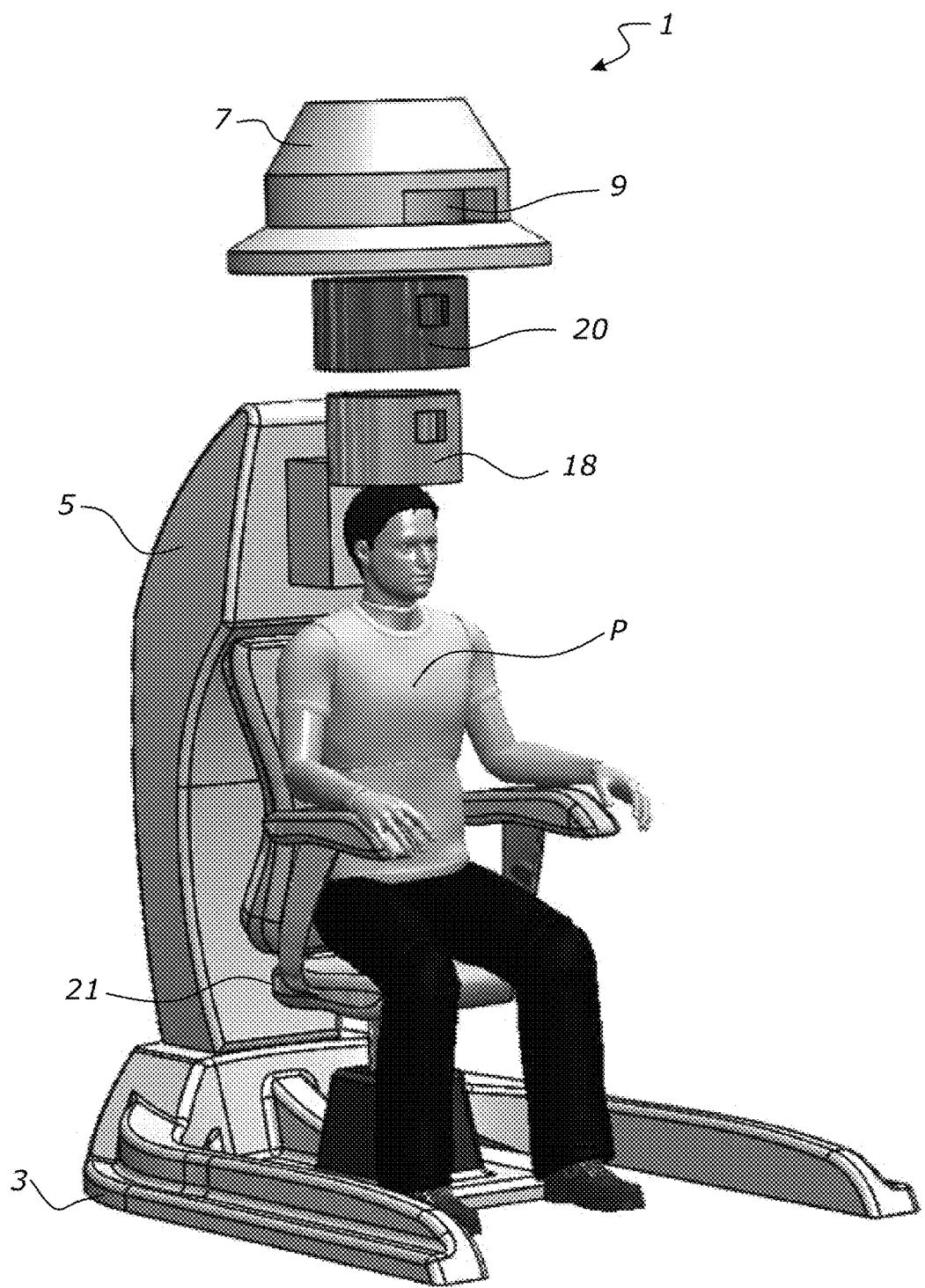
FIG. 3 is a perspective view similar to FIG. 2, but showing an exploded view of the apparatus.
Figure 4:
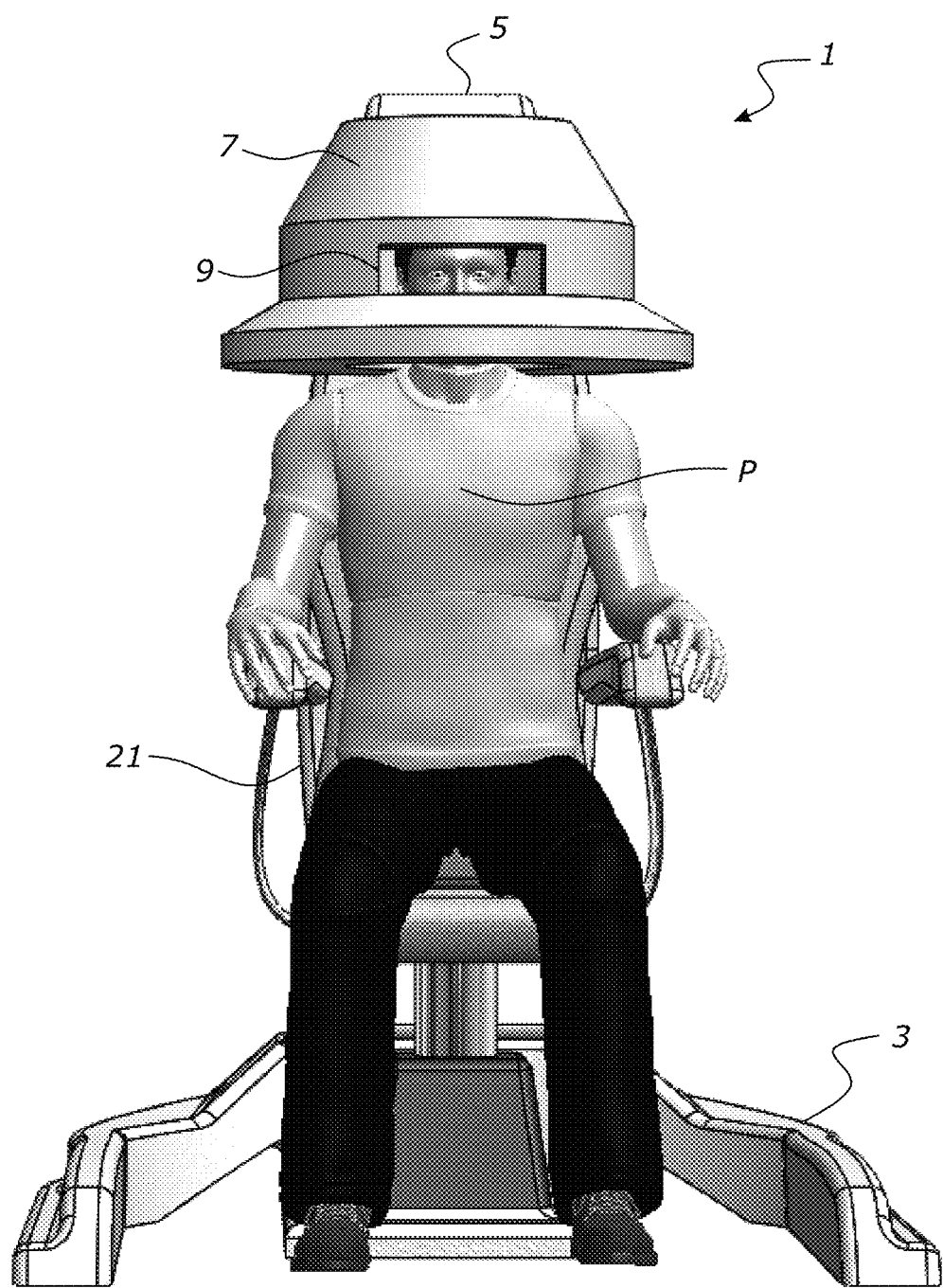
FIG. 4 is a front view similar to FIG. 2.
Figure 5:
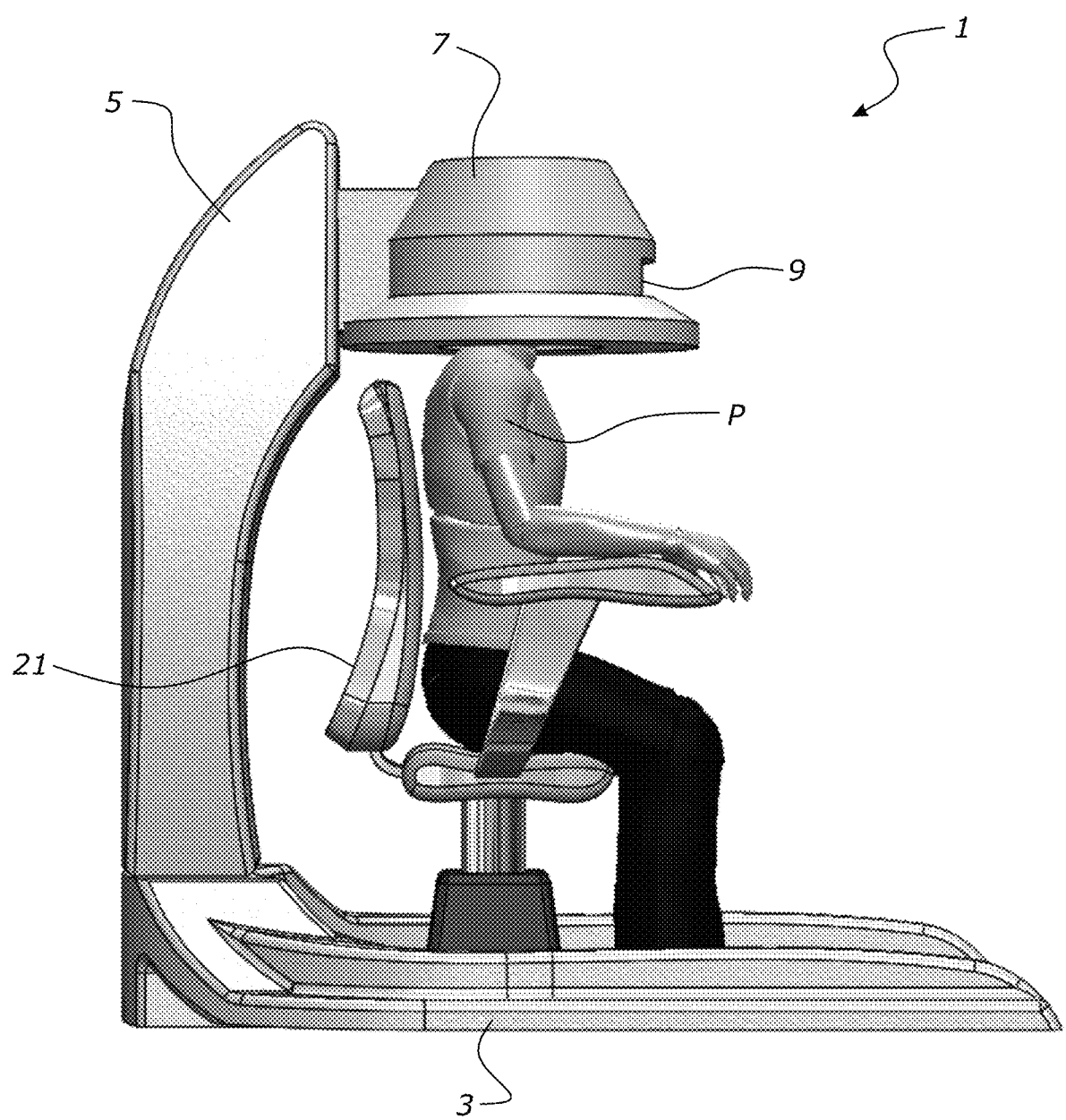
FIG. 5 is a side view similar to FIG. 2.

Referring to FIG. 3, the MRI apparatus 1 also comprises a radio frequency (RF) coil assembly 18, and a gradient coil 20. Not illustrated but provided are suitable RF and gradient amplifiers and a spectrometer to control the MRI apparatus. FIG. 3 shows how the RF coil assembly 18 and the gradient coil 20 may be positioned relative to the magnet. The RF coil assembly 18 is used to transmit RF pulses and hence excite spin magnetization within the imaging volume according to the requirements of the particular MRI pulse sequence. The gradient coil 20 applies pulsed field gradients in at least two planes to encode the region within the imaging volume that is to be imaged. The spectrometer synchronises the gradient and RF pulses and performs the signal acquisition according to the requirements of the particular MRI pulse sequence. The RF and gradient amplifiers amplify the gradient and RF signals from the spectrometer. The RF pre-amplifier(s) amplify the MRI signal before reception into the spectrometer.

The RF coil assembly 18, gradient coil 20, amplifiers and spectrometer are used in the generation of pulse sequences for obtaining MRI images. Suitable pulse sequences are discussed in more detail later in the specification.

Magnet

FIGS. 6(a)-(e) show a simplified view of an exemplary magnet 7 for use in the apparatus 1. The magnet 7 is an asymmetric magnet, and comprises a plurality of superconducting coils that are positioned around a cylindrical axis 29 and spaced along said axis to provide a magnetic field on the cylindrical axis. The magnet 7 comprises a patient end 23 arranged to be positioned adjacent or against a patient's shoulders 31 with the patient's shoulders 31 outside the magnet 7, as shown in FIGS. 2, 4, 5, and 6(e). The patient end 23 may be positioned slightly above a patient's shoulders 31 or may contact the top of the patient's shoulders 31. The magnet 7 further comprises a recess 27 for receipt of the patient's head 33 and extending into the magnet 7 from the patient end 23 as shown in FIGS. 6(d) and 6(e). The magnet recess 27 has a transverse dimension (e.g. diameter) that is smaller than the width of a patient's shoulders.

Figure 6:
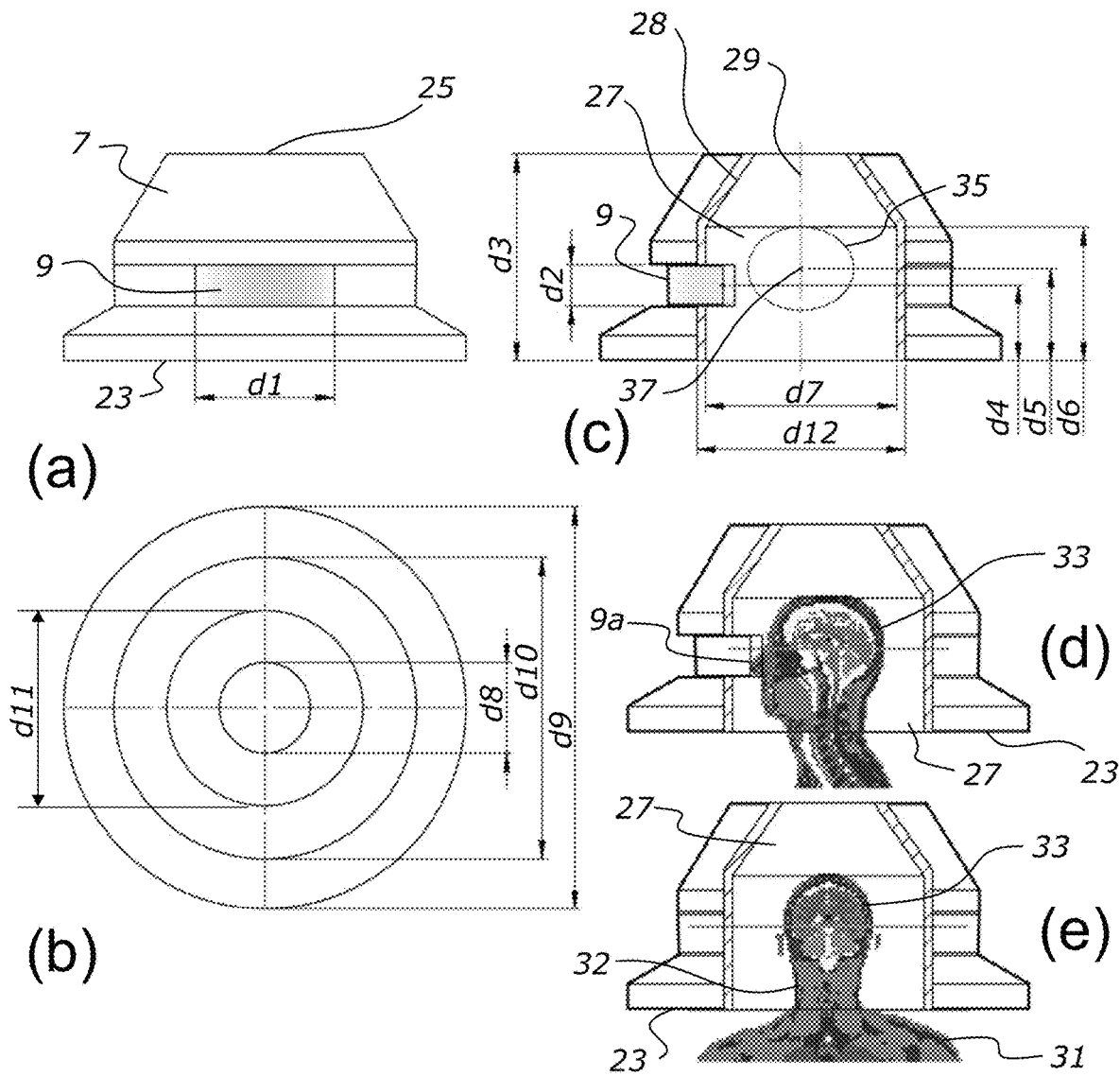
FIG. 6 is a simplified view of the magnet of the apparatus of FIG. 1, where

The magnet 7 is configured to provide an offset imaging volume 35 in the recess 27 as shown in FIG. 6(c). The imaging volume has an isocentre that is closer to the patient end of the magnet than to the opposite end of the magnet. In the embodiment shown in FIG. 6, the imaging volume 35 has an isocentre 37 that is positioned less than about 170 mm from the patient end 23 of the magnet to accommodate the relative height of the head and shoulders of most human adults, to align the isocentre 37 with the centre of the patient's brain. In an embodiment, the isocentre 37 is positioned less than about 169 mm from the patient end 23, or less than about 168 mm from the patient end 23, or at about 167 mm from the patient end 23 of the magnet 7. Positioning the isocentre at about 167 mm from the patient end is believed to enable 90% of the population to have their shoulders outside the apparatus. In an embodiment, the isocentre 37 is positioned more than about 130 mm from the patient end 23, or more than about 140 mm from the patient end 23, or more than about 150 mm from the patient end 23, or more than about 160 mm from the patient end 23.

The magnet 7 is configured to only receive the patient's head 33 and optionally part of the patient's neck 32, such that the magnet 7 is configured for use as part of a head-only MRI apparatus 1. The magnet 7 is configured to provide an imaging volume 35 that is sized and positioned to overlay a typical adult patient's brain. The imaging volume 35 is a substantially ellipsoidal shape, having a relatively large transverse dimension and a relatively short dimension along the cylindrical axis.

The magnet 7 defines a cylindrical axis 29. The recess 27 and the imaging volume 35 are coaxial with the cylindrical axis 29. The imaging volume 35 is positioned closer to the patient end 23 of the magnet 7 than to an opposite end 25 of the magnet, along the cylindrical axis 29.

In an embodiment, the magnet 7 has a length from the patient end 23 to the opposite 25 end of less than about 400 mm, or of less than about 390 mm, or of less than about 385 mm, or of less than about 380 mm, or of less than about 375 mm, or of about 374 mm. In the embodiment shown in FIG. 6, the magnet 7 has a length from the patient end 23 to the opposite end 25 of 374 mm. In an embodiment, the magnet 7 has a length from the patient end 23 to the opposite end 25 of more than about 350 mm. In other embodiments, the length may be longer or shorter.

The magnet 7 comprises a window 9 to enable a patient to see out of the magnet 7 when their head 33 is positioned in the recess 27. The window 9 comprises an opening that extends through a wall of the magnet 7 from the recess 27 to an exterior of the magnet 7. In an embodiment, the window 9 comprises an at least partially transparent material 9a that covers at least part of the opening, such as glass or a polymer material. In an embodiment, the magnet is part of a Faraday cage and the window covering 9a comprises a conductive material such as copper mesh, indium tin oxide, a conductive polymer or glass coated in a transparent conductor. In an embodiment, the magnet 7 does not have a window.

The magnet may comprise passive shims 28. Passive shims 28 are formed from a ferromagnetic material and may be used to correct for the difference in homogeneity between designed and as-built magnetic fields.

Exemplary dimensions for one possible configuration of the magnet 7 are provided below. It will be appreciated that other configurations are within the scope of the invention.

Window 9: d1=250 mm in the transverse direction, d2=75 mm in the vertical direction.

Total height of magnet 7: d3=374 mm in the vertical direction.

Height of centre of window 9: d4=137 mm from the patient end 23 of the magnet 7.

Height of isocentre 37 of imaging volume 35: d5=167 mm from the patient end 23 of the magnet 7.

Height of cylindrical portion 75: d6=242 mm from the patient end 23 of the magnet 7.

Inner diameter of the bottom of the recess 27: d7=345 mm.

Inner diameter of the top of the recess 27: d8=164 mm.

Outer diameter of the bottom part of the magnet 7: d9=725 mm.

Outer diameter of the middle part of the magnet: d10=585 mm.

Outer diameter of the top part of the magnet: d11=403 mm.

Inner diameter of the coil pack 41: d12=375 mm.

Figure 7:
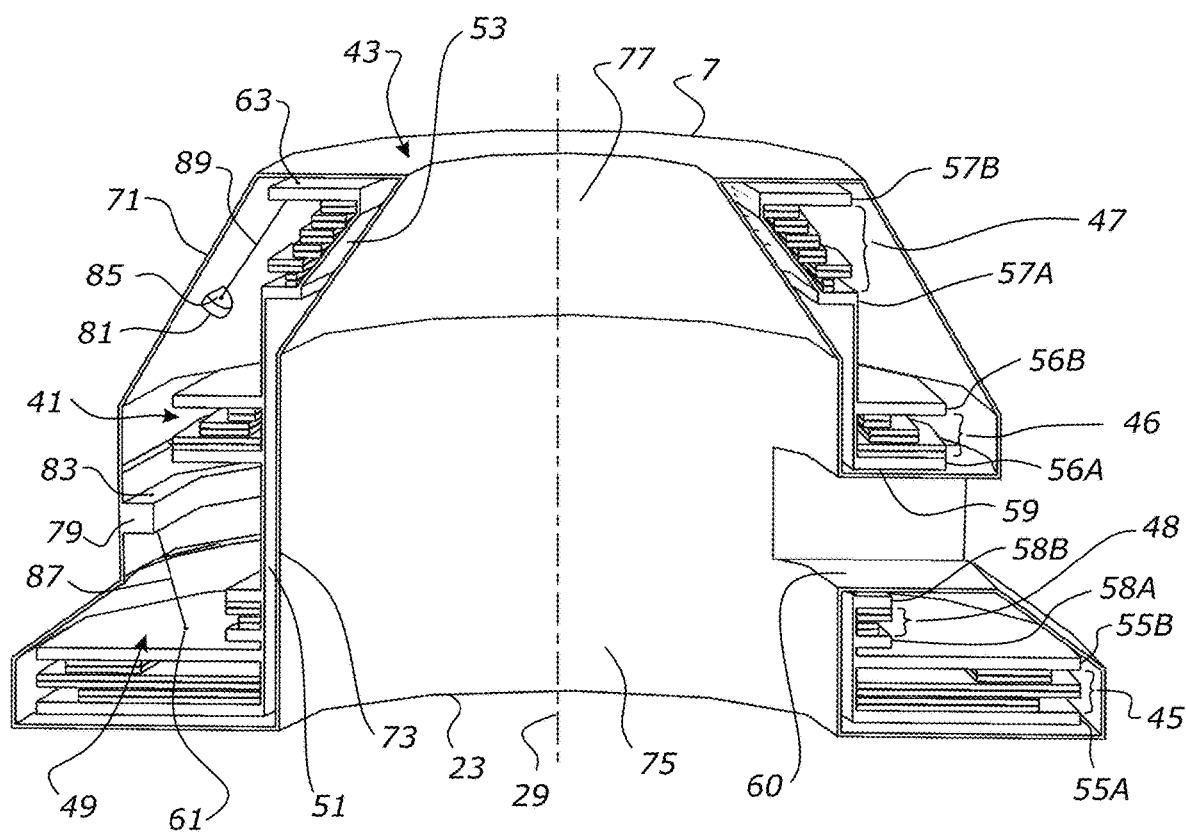
FIG. 7 is a sectional perspective view of the magnet.

FIG. 7 shows a detailed cross-sectional view of the magnet 7. The magnet 7 comprises a coil pack 41 suspended within a cryostat 43. In an embodiment, no isothermal radiation shield is provided between the coil pack 41 and the room temperature surfaces of the magnet 7, so that the lowest coils can be positioned close to the patient end 23 of the magnet 7 to provide a compact magnet.

Coil Pack

The coil pack 41 comprises four groups of coils 45, 46, 47, 48 mounted on a coil former 49. The coil former 49 prevents coil movement or deflection under normal operating circumstances. The coil former 49 may be made from a non-ferrous material such as stainless steel.

The coil pack 41 is wrapped in a low emissivity material (not shown) to limit the radiation heat load onto the coil pack 41 in place of an isothermal radiation shield. In an embodiment, the low emissivity material is multi-layer insulation, such as RUAG Coolcat.

Coil Former

An exemplary coil former 49 comprises a generally cylindrical lower portion 51 and a frustoconical upper portion 53. Three pairs of annular flanges 55A, 55B, 56A, 56B, 58A, 58B, extend outwardly from the cylindrical portion 51. One pair of annular flanges 57A, 57B extends outwardly from the frustoconical portion 53. In the embodiment shown in FIG. 7, the annular flange 57A also functions as a connecting member between the cylindrical portion 51 and the frustoconical portion 53. It will be appreciated that in alternative embodiments the cylindrical portion 51 may directly connect to the frustoconical portion 53 and that a different number of annular flanges may be used.

Each pair of annular flanges is adapted to receive one or more superconducting coils.

One or more shims (not illustrated) made from an insulating material may be used to correctly position the coils on the coil former.

The cylindrical portion 51 of coil former 49 comprises a substantially rectangular slot 59 that corresponds to the window 9 of the magnet 7. Two pairs of annular flanges 55A, 55B, 58A, 58B are located below the slot 59. Two pairs of annular flanges 56A, 56B, 57A, 57B are located above the slot 59.

At least two flanges comprise a series of apertures or couplings that may be used for supporting/suspending the coils as discussed in more detail below. In the embodiment shown in FIG. 7, the top flange 57B and the second to bottom flange 55B each comprise a series of apertures 61, 63. In an embodiment, each flange comprises eight apertures 61, 63. It will be appreciated that any suitable number of apertures may be used.

A skilled person will appreciate that the coil former could have a different configuration, and the coils could be formed/supported in a different way.

Coils

Figure 8:
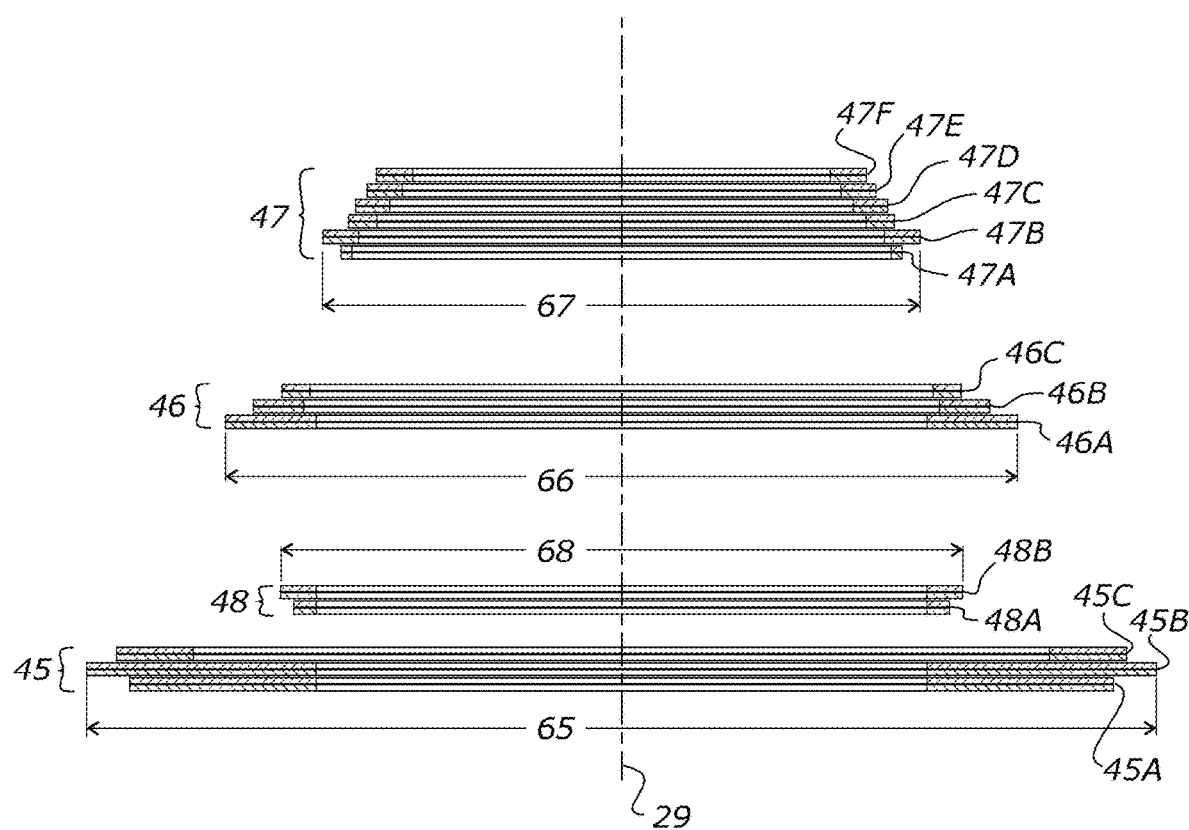
FIG. 8 is a sectional side view of an exemplary arrangement of coils of the magnet.

FIG. 8 shows a sectional side view of an exemplary arrangement of the superconducting coils 45A-C, 46A-C, 47A-F, 48A-B of the magnet 7. The coils 45A-C, 46A-C, 47A-F, 48A-B are annular coils that surround the recess 27. The coils are coaxial with the cylindrical axis 29.

The magnet 7 comprises at least three groups of coils. The coils have a generally tapering arrangement. In the embodiment shown in FIG. 8, the magnet 7 comprises a first group of coils 45 positioned at or toward the patient end 23 that has a first relatively large transverse outer dimension 65, a second group of coils 46 positioned further from the patient end 23 that has a second relatively small transverse outer dimension 66, and a third group of coils 47 positioned at or toward the opposite end that has a third transverse outer dimension 67 that is smaller than the second transverse outer dimension 66.

The first 45, second 46, and third 47 groups of coils are arranged to provide a summation of magnetic field from the first 45, second 46, and third 47 group of coils and provide a magnetic field in a first sense. For example, the first 45, second 46, and third 47 groups of coils have the same winding direction, e.g. a positive or clockwise winding direction, to provide a summation of magnetic field from the first 45, second 46, and third 47 group of coils.

In an embodiment, the magnet 7 comprises at least one additional group of coils that is arranged to provide a magnetic field in a second sense that is opposite to the first sense. For example, the at least one additional group of coils may have a winding direction opposite to the first 45, second 46, and third 47 groups of coils, e.g. a negative or anticlockwise winding direction. As another example, all coils may be wound in the same direction but the at least one additional group of coils may be operatively connected to receive current in an opposite sense to the current that is received by the first 45, second 46, and third 47 groups of coils.

In the embodiment shown in FIG. 8, the magnet 7 has one group of coils, the fourth group 48, that provides magnetic field in a second sense that is opposite to the first sense. The fourth group of coils 48 is positioned between the first group of coils 45 and the second group of coils 46. The fourth group of coils 48 has a transverse outer dimension 68 that is smaller than the transverse outer dimension 65 of the first group of coils 45 and the transverse outer dimension 66 of the second group of coils 46. The magnet 7 could alternatively have two or more groups of coils with an opposite winding direction. The two or more groups could, for example, be located at different axial positions in the magnet.

Exemplary coil dimensions are provided in table 1.

TABLE 1 exemplary coil dimensions

| Coil number | Inner diameter (mm) | Outer diameter (mm) | Axial position (to centre of respective double pancake) from isocentre (mm) |
|---|---|---|---|
| 47F | 135.2 | 158.5 | 185 |
| 47E | 142.1 | 164.6 | 175 |
| 47D | 150.1 | 172.2 | 165 |
| 47C | 158.3 | 176.6 | 155 |
| 47B | 170.1 | 193.2 | 145 |
| 47A | 174.4 | 181.5 | 135 |
| 46C | 201.6 | 219.6 | 45 |
| 46B | 205.6 | 238.1 | 35 |
| 46A | 197.6 | 256.1 | 25 |
| 48B | 197.5 | 220.5 | −85 |
| 48A | 197.5 | 212.0 | −95 |
| 45C | 277.0 | 326.8 | −125 |
| 45B | 197.7 | 346.0 | −135 |
| 45A | 197.5 | 318.3 | −145 |

The inner diameters of at least one of the groups of coils, for example the top group of coils, may follow a generally arcuate path. The apparatus may have more groups of coils.

The number and position of the coils are determined so as to minimise the length of conductor in light of the ergonomic and homogeneity constraints of the magnet. The exemplary magnet shows how this may be achieved for the constraints used to define this magnet. It will be apparent to those skilled in the art that alternative configurations are possible depending on the specific constraints of the magnet which is desired. For example, a fewer or greater number of coils may be required. Alternatively, the same coil axial positions could be utilised, whilst changing the inner and outer diameter of the coils. Finally, the same number of coils could be used whilst adjusting the coil axial positions and the coil inner and outer diameters. For example, at least one of the groups of coils could consist of one coil. For example, all of the groups of coils could each consist of one coil. The coil may comprise LTS material. As another example, at least one of the groups of coils could consist of a plurality of coils. For example, all of the groups of coils could each consist of a plurality of coils. The plurality of coils may comprise HTS material.

The coil arrangement provides the asymmetric positioning of the isocentre along the cylindrical axis.

The isocentre is positioned so that a bottom edge of the imaging volume is not positioned lower than the bottom of the first group of coils.

In an embodiment, the isocentre is positioned less than about 165 mm above a patient end of the first group of coils, optionally less than about 160 mm above the patient end of the first group of coils, optionally at about 157 mm above the patient end of the first group of coils, optionally less than about 157 mm above the patient end of the first group of coils. In an embodiment, the isocentre is positioned more than about 75 mm above the patient end of the first group of coils.

In an embodiment, the isocentre is positioned less than about 200 mm below a top of the third group of coils, optionally less than about 195 mm below the top of the third group of coils, optionally less than about 190 mm below the top of the third group of coils, optionally at about 189 below the top of the third group of coils.

The inner and outer diameters of the coils 45A-C, 46A-C, 47A-F, 48A-B are generally smaller for the coils that are further away from the patient end 23 of the magnet 7. This reduces magnet size and minimises conductor usage.

In an embodiment, at least some of the coils comprise double pancake coils. In an embodiment, substantially all of the coils comprise double pancake coils. Additionally or alternatively, at least some of the coils may comprise layer-wound coils.

In the embodiment shown in FIGS. 7 and 8, all of the coils 45A-C, 46A-C, 47A-F, 48A-B comprise double pancake coils. Double pancake coils comprise two single pancake coils wound around a common axis. The single pancakes in the double pancake coil may share one or more conductors. The two single pancake coils are separated from each other by a thin layer of insulating material. The double pancake coils are insulated top and bottom. Double pancake coils may be stacked up into a group with annular cooling plates between adjacent double pancake coils to allow extraction of heat to the refrigeration source.

Each of the coils of the double pancake or layer wound coil may have an intermediary layer between turns, such as stainless steel, copper or an insulator. It will be appreciated to those skilled in the art that tuning the electrical conductivity of this layer will change the ramping time and quench characteristics of the coil. For double pancake coils wound from REBCO, stainless steel protects the coils against the risk of quench, while avoiding long magnet settling times associated with using a copper intermediary layer. Alternatively, insulation may be used between turns and the magnet quench protected using alternative methods.

In an embodiment, the superconducting coils comprise low temperature superconducting (LTS) material. In an embodiment, the coils comprise Niobium-Tin ($Nb_3Sn$) material or Niobium-Titanium (NbTi) material.

In an embodiment, the coils comprise a superconductive material with a critical temperature that is greater than 20 K. Such a material requires cooling to a higher temperature than LTS materials to achieve superconducting properties. In an embodiment, the coils comprise Magnesium Diboride ($MgB_2$) material.

In an embodiment, the coils comprise high temperature superconducting (HTS) material. In an embodiment, the coils comprise rare-earth barium copper oxide (REBCO) material or Bismuth-Strontium-Calcium-Copper-Oxide (BSCCO) material.

The coils may be wound from a tape of superconductive material. The tape may be laminated with a conductive material. For example, the coils may be wound from a REBCO tape that is laminated with stainless steel.

In an embodiment, each double pancake coil 45A-C, 46A-C, 47A-F, 48A-B is about 10 mm high, including the two coils, the insulation layer, and a cooling plate. Each coil in the pancake may be about 4 mm high. The thickness and dimensions may vary.

HTS material requires cooling to a higher temperature than LTS material to achieve superconducting properties. Conventional MRI machines utilise LTS materials that typically require cooling to around 4.2 K. By contrast, use of REBCO HTS material allows the magnet 7 to run at around 35 K to achieve around 1.5 T operation.

Higher temperature operation may provide several advantages. Conventional MRI machines typically require isothermal radiation shielding and cryogen baths to achieve the required cooling for LTS material.

The exemplary materials described above are by way of example only and the coils may be formed from any suitable superconducting material.

In the embodiment shown in the figures, no isothermal radiation shield is provided between the coil pack 41 and room temperature surfaces of the magnet 7. This allows the magnet 7 to be more compact and the isocentre 37 of the imaging volume 35 to be located closer to the patient end of the magnet.

Cryostat

The cryostat 43 is a vessel suitable for supporting a high vacuum. The cryostat 43 has suitable penetrations (not shown) for applying vacuum, injecting current and accommodating the cryocooler 19. The cryostat is made, for example, from stainless steel.

The cryostat 43 comprises a vacuum manifold (not illustrated). The cryocooler 19 (shown in FIG. 1) interfaces with the cryostat 43 via the vacuum manifold. The cryocooler is positioned with a portion outside the vacuum manifold in a relatively warm region and a portion inside the vacuum manifold in the cool region. Conductors such as thermally conductive strips, heat pipe, or other conductors are used to transfer heat away from the coils via the cryocooler.

Referring to FIG. 7, the cryostat 43 has an outer shell 71, an inner shell 73 and a slot 60. The inner shell 73 comprises a generally cylindrical lower portion 75 and a frustoconical upper portion 77. The outer shell 71 is shaped to accommodate the shape of the coil pack 41 and has a frustoconical lower portion, a generally cylindrical intermediate portion, and a frustoconical upper portion. The inner shell 73 and the outer shell 71 are both sized to accommodate the coil pack 41 such that the coil pack 41 does not contact the cryostat 43.

An annular ledge 79 runs around a substantial portion of the inner face of the outer shell 71. In an embodiment, the annular ledge 79 is made from the same material as the cryostat 43. The annular ledge 79 may be integrally formed as part of the cryostat 43. Alternatively, the annular ledge may be a separate part that is welded to the inner face of the outer shell 71.

In an alternative embodiment, multiple shorter ledges or lugs are used instead of a single continuous ledge. The shorter ledges or lugs may be integrally formed as part of the cryostat 43. Alternatively, the shorter ledges or lugs may be a separate part that is welded to the inner face of the outer shell 71.

The cryostat 43 also has lugs 81 spaced around the inner face of the outer shell 71. The lugs 81 are positioned further from the patient end 23 of the magnet 7 than the ledge 79 is. In an embodiment, the lugs 81 are made from the same material as the cryostat 43 and are welded to the cryostat 43. The lugs 81 may be integrally formed as part of the cryostat 43. Alternatively, the lugs may be a separate part that is welded to the inner face of the outer shell 71.

In an alternative embodiment, an annular ledge that runs around a substantial portion of the inner face of the outer shell 71 is used instead of the lugs 81. The annular ledge may be integrally formed as part of the cryostat 43. Alternatively, the annular ledge may be a separate part that is welded to the inner face of the outer shell 71.

The annular ledge 79 and lugs 81 comprise a series of apertures or couplings 83, 85. In an embodiment, the annular ledge 79 comprises eight apertures 83 and the cryostat comprises eight lugs 81 each with an aperture 63. It will be appreciated that any suitable number of apertures and lugs may be used. The coil pack 41 is suspended between the apertures or couplings 83, 85, by interweaving a series of tension members 87, 89 of a high tensile strength, low thermal conductivity material through the apertures or couplings 83, 85. An exemplary material for the tension members 87, 89 is Kevlar. It will be appreciated that other suitable high tensile strength, low thermal conductivity materials may be used.

Tension members 87, 89 suspend the coil former 41 and thereby the superconducting coils 45A-C, 46A-C, 47A-F, 48A-B in close proximity to the walls of the cryostat 43, reducing the potential for coupling vibration into the magnet and minimising the potential for changes in magnet homogeneity during transport.

Cryocooler

Using HTS material means that a highly efficient single stage cryocooler 19 may be used to cool the magnet via conduction instead of the cryogen bath typically required by LTS MRI machines. This may provide several advantages. LTS MRI machines typically use a liquid helium cryostat. A liquid helium cryostat adapted for use with an apparatus having a window would be extremely complex. Liquid helium cryostats are also impractical to move. Cryocoolers are comparatively simple and portable. Use of a cryocooler means the magnet is cryogen-free and can be comparatively easily relocated, and may be used in situations or environments that are not possible for a conventional MRI machine, such as in emergency rooms, mobile neuro-scanning clinics, or other environments.

The cryocooler may be a single stage cryocooler or a two stage cryocooler.

The magnet may have a cool-down time of around one to two days and a tolerance in the order of magnitude of 10 W of heat load into the magnet cryostat during steady-state operation.

It is estimated that the magnet 7 will operate at 170 A. There will be an additional estimated 15 W of load resulting from radiation and conduction heat loads on the cryocooler.

The cryocooler may be any suitable commercially available cryocooler. For example, a single stage Sumitomo Heavy Industries CH-110 cryocooler gives 70 W of cooling at 35 K, which is ample to cool the magnet to the proposed operating temperature.

Imaging Volume

The imaging volume 35 comprises relatively low uniformity of more than about 200 ppm and up to about 4000 ppm field variation over the imaging volume. In an embodiment, the imaging volume comprises relatively low uniformity of more than about 500 ppm and up to about 4000 ppm field variation over the imaging volume. In an embodiment, the imaging volume comprises relatively low uniformity of more than about 1000 ppm and up to about 4000 ppm field variation over the imaging volume. In an embodiment, the imaging volume comprises relatively low uniformity of more than about 1000 ppm and up to about 3000 ppm field variation over the imaging volume. The imaging volume is substantially ellipsoidal in shape. In an embodiment, the imaging volume has a length of about 150 mm and a transverse dimension of about 190 mm.

The magnet 7 is configured to provide an imaging volume 35 that is positioned along a cylindrical axis 29 of the magnet 7 in the recess.

Figure 9:
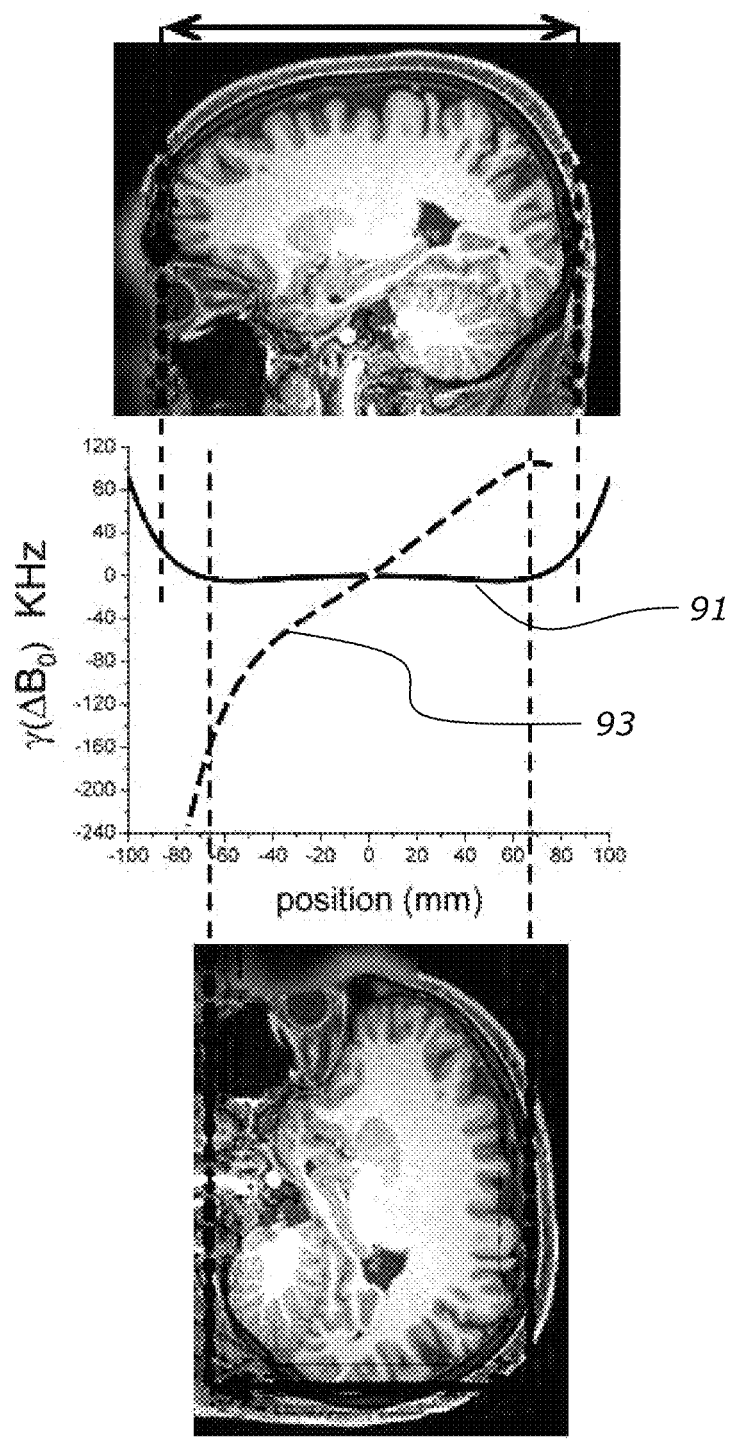
FIG. 9 is a chart showing the magnetic field profile across the imaging volume in the transverse direction and along the cylindrical axis of the magnet.

FIG. 9 shows exemplary magnetic field variation in a forward-to-rearward direction of the patient's brain (plot 91) and in a bottom-to-top direction of the patient's brain (plot 93). At least a major part of the imaging volume in the forward-to-rearward direction has a substantially zero magnetic field gradient 91 in a radial direction. At least a major part of the imaging volume in the bottom-to-top direction has a substantially linear non-zero magnetic field 93 gradient along the cylindrical axis 29.

The substantially non-zero magnetic field gradient is static, and may be used as the readout gradient for the MRI imaging sequence when the MP-SSFP pulse sequence is used (described in more detail below). Typically, three pulsed gradient channels are required for MRI imaging. Use of the non-zero magnetic field gradient as part of the MRI imaging sequence requires only two pulsed gradient channels, providing for simpler operation and control of the apparatus In an embodiment, at least about 75% of the imaging volume has a substantially linear magnetic field gradient along the cylindrical axis, optionally at least about 80% of the imaging volume has a substantially linear magnetic field gradient along the cylindrical axis, optionally at least about 85% of the imaging volume has a substantially linear magnetic field gradient along the cylindrical axis, optionally about 86% of the imaging volume has a substantially linear magnetic field gradient along the imaging volume, and optionally substantially the entire imaging volume has a substantially linear magnetic field gradient along the imaging volume.

In the embodiment shown in the figures, the magnetic field 93 generally increases in a direction from the patient end to an opposite end of the magnet, along the cylindrical axis. In an alternative embodiment, the magnetic field 93 generally decreases in a direction from the patient end to an opposite end of the magnet, along the cylindrical axis. For example, the magnetic field may be a mirror image of the magnetic field 93 shown in FIG. 9.

Shielding

In an embodiment, the MRI apparatus 1 further comprises magnetic shielding. Magnetic shielding limits the distance the magnetic field extends into the space surrounding the magnet 7. Standard shielding requirements require that no member of the public is exposed to a magnetic field greater than 5 Gauss (0.5 mT) without warning. In practice, the 5 Gauss line of the magnet 7 determines the size of the room that the magnet 7 is installed in. Shielding is advantageous because shielded magnets can be installed in smaller rooms. However, shielding is not essential to the operation of the magnet.

Figure 10A:
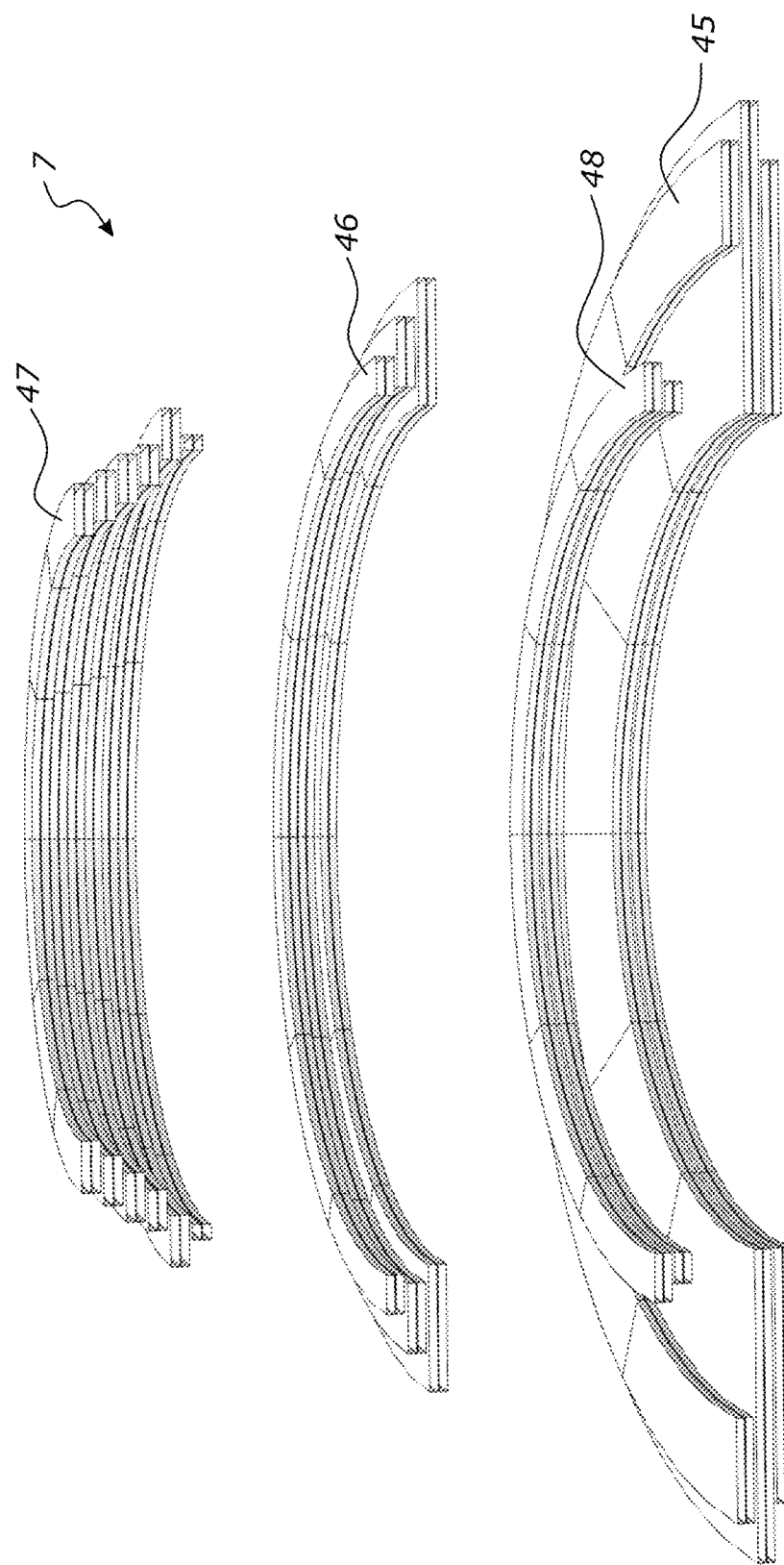
FIG. 10(a) is a perspective sectional view of the magnet with no shielding cut through the Y-Z plane.
Figure 10B:
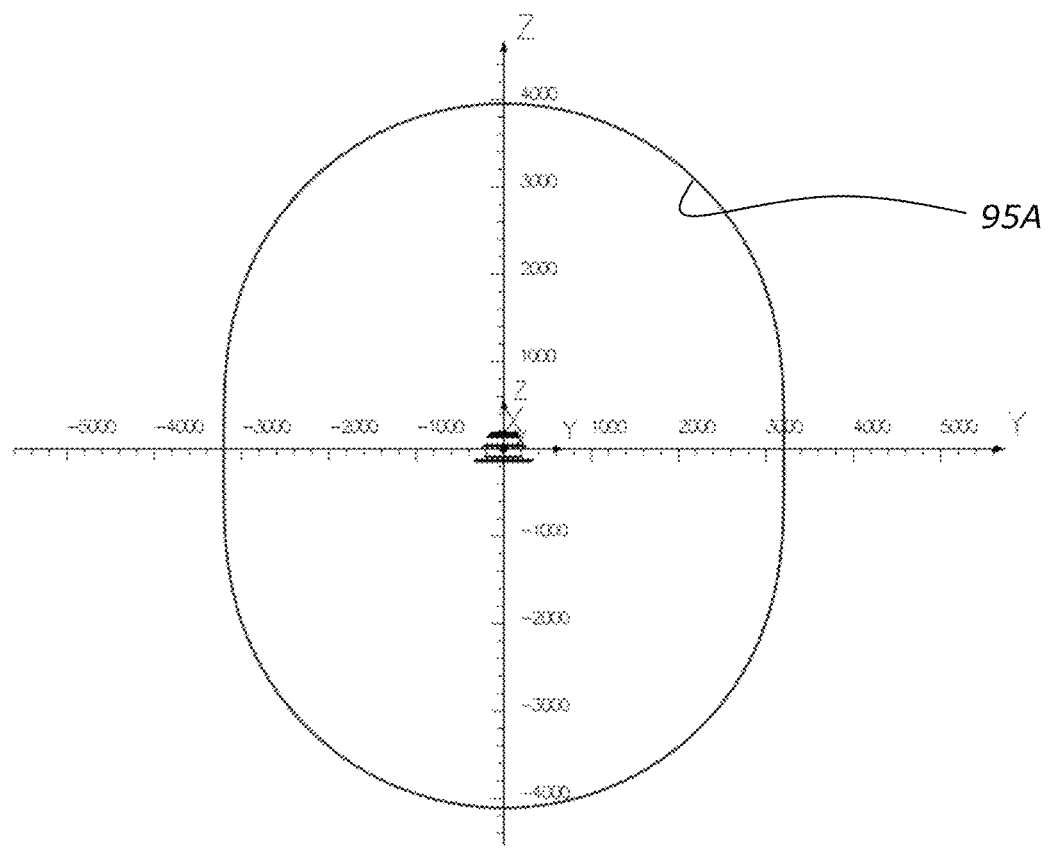
FIG. 10(b) is a graph that shows the 5 Gauss line corresponding to the unshielded magnet in the Y-Z plane.
Figure 10C:
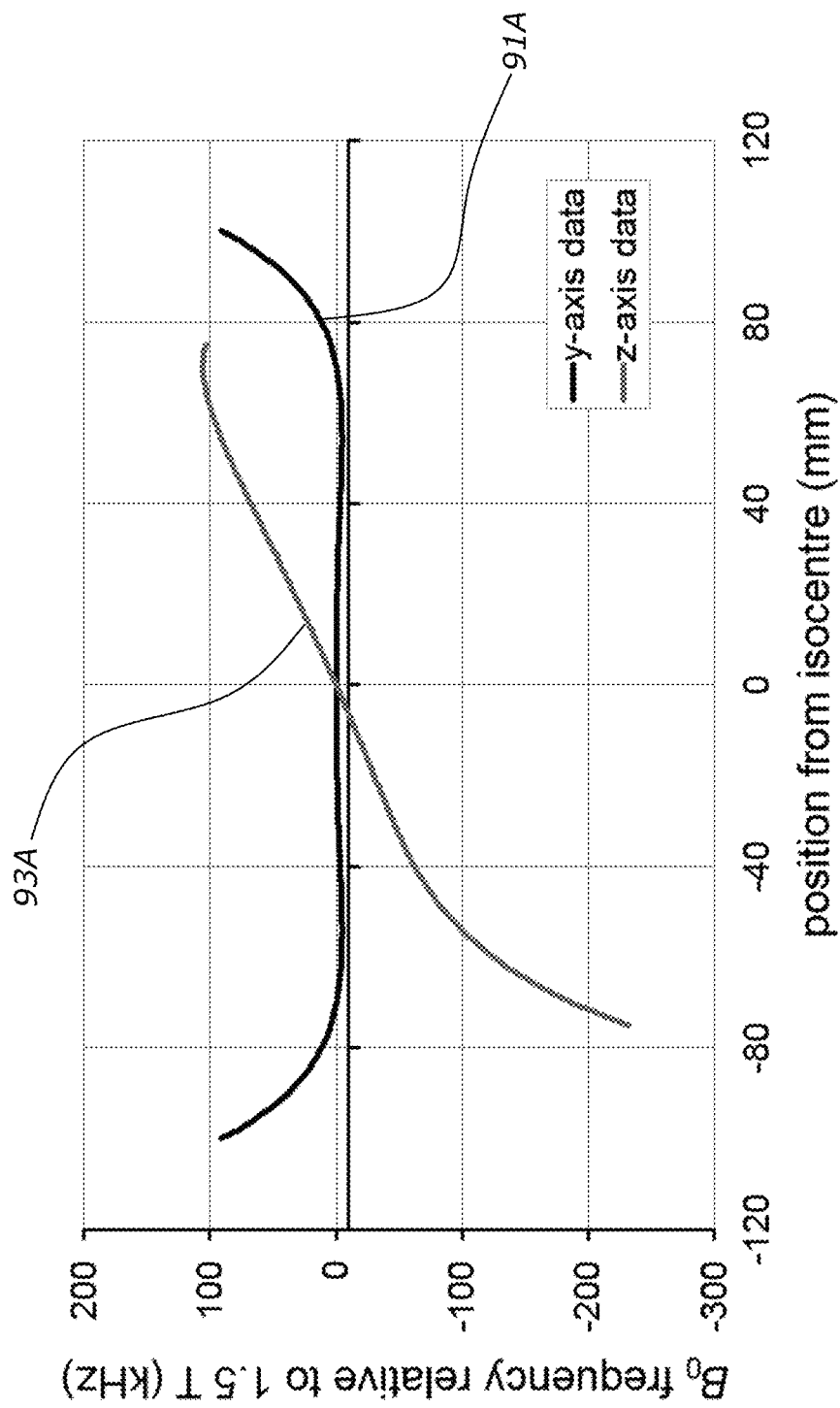
FIG. 10(c) is a graph of the magnetic field variation across the imaging volume for the unshielded magnet.

FIG. 10(*a*) shows a perspective sectional view of the magnet 7 cut through the Y-Z plane. FIG. 10(*b*) shows the 5 Gauss line 95A corresponding to the unshielded magnet in the Y-Z plane. The 5 Gauss line extends about 3 m from the centre of the magnet 7 in the Y direction and about 4 m from the centre of the magnet 7 in the Z direction. FIG. 10(*c*) shows the magnetic field variation across the imaging volume for the unshielded magnet 7. Plot 91A shows the magnetic field variation in the Y direction (forward-to-rearward). Plot 93A shows the magnetic field variation in the Z direction (bottom-to-top).

As discussed above in relation to FIG. 9, at least a major part of the imaging volume in the forward-to-rearward direction has a substantially zero magnetic field gradient 91A in a radial direction. At least a major part of the imaging volume in the bottom-to-top direction has a substantially linear non-zero magnetic field gradient 93A along the Z (cylindrical) axis.

Figure 11A:
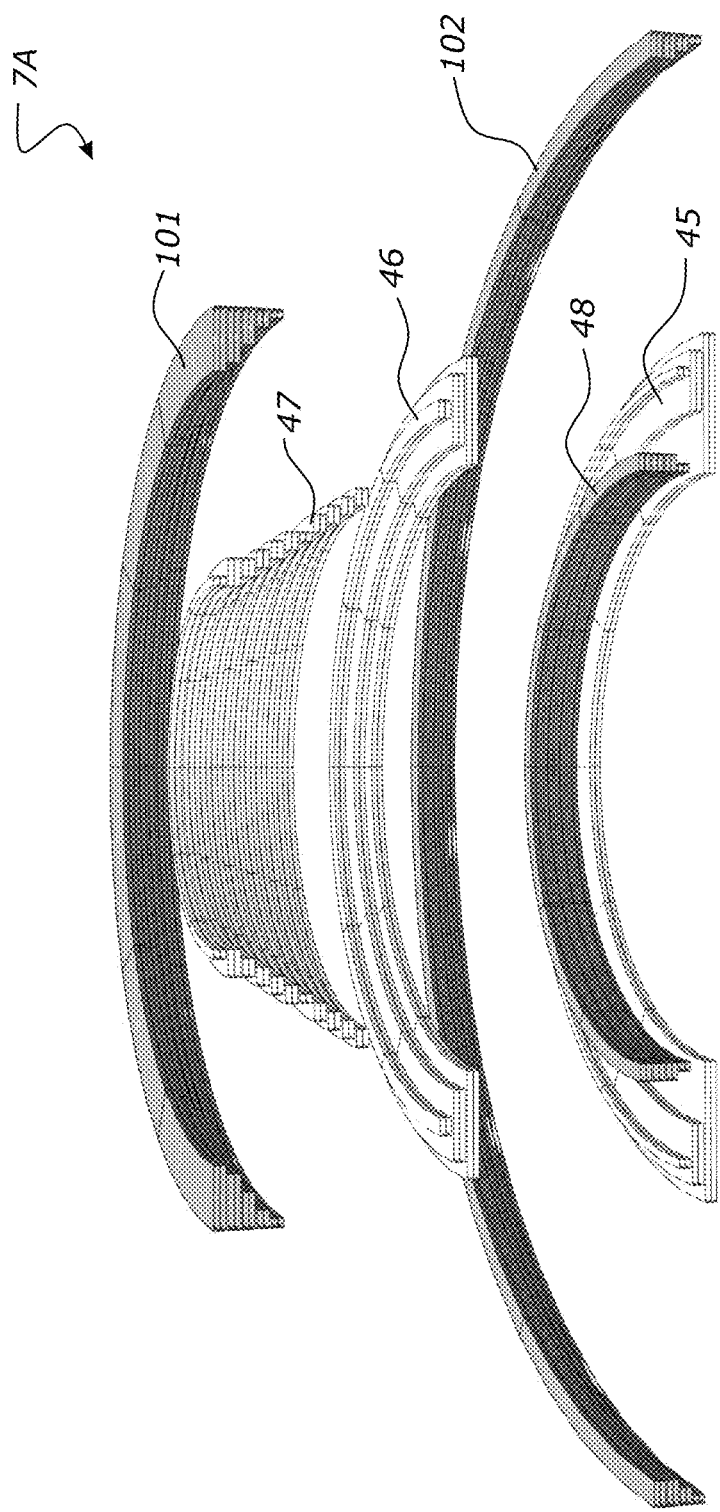
FIG. 11(a) is a perspective sectional view of an actively shielded magnet cut through the Y-Z plane.

In an embodiment, the MRI apparatus 1 comprises active magnetic shielding. FIG. 11(a) shows a perspective sectional view of an actively shielded magnet 7A cut through the Y-Z plane. The magnet 7A comprises additional groups of coils 101, 102 positioned radially outward of the main groups of coils 45, 46, 47, 48 that generate the main magnetic field in the imaging volume. The additional groups of coils 101, 102 are wound in an opposite sense relative to the main groups of coils 45, 46, 47 and act as a return path for the magnetic flux from the magnet 7A.

In an embodiment, at least one of the additional groups of coils consists of one coil. In an embodiment, all of the additional groups of coils each consist of one coil. The coil may comprise LTS material.

In an embodiment, at least one of the additional groups of coils consists of a plurality of coils. In an embodiment, all of the additional groups of coils each consist of a plurality of coils. The plurality of coils may comprise HTS material.

The additional groups of coils 101, 102 also influence the magnetic field in the imaging volume. It is necessary to modify the design of the main groups of coils 45, 46, 47, 48 to account for the effect of the additional groups of coils 101, 102 in order to achieve the desired field gradient in the imaging volume. FIG. 11(a) shows one possible active shielding arrangement. Other arrangements are envisaged and this example is non-limiting.

Figure 11B:
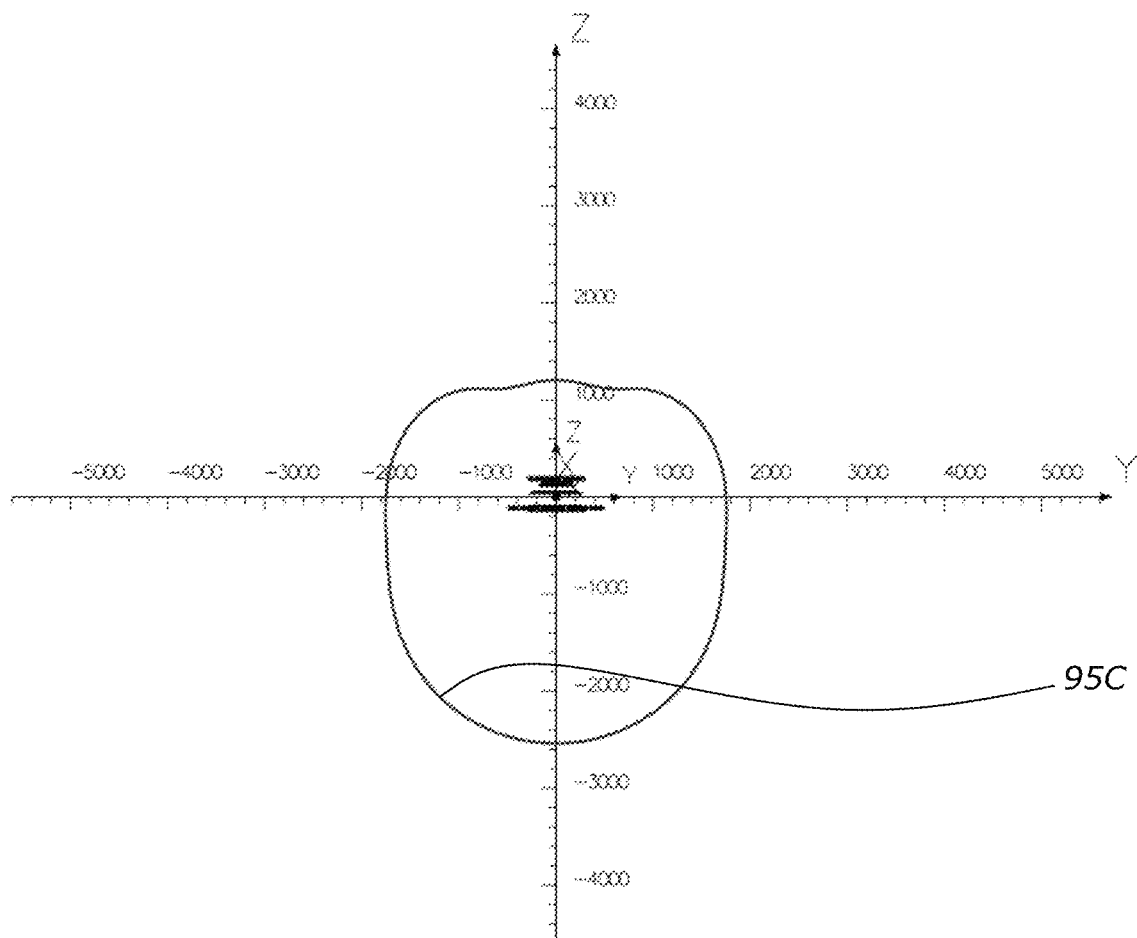
FIG. 11(b) is a graph that shows the 5 Gauss line corresponding to the actively shielded magnet in the Y-Z plane.

FIG. 11(b) shows the 5 Gauss line 95C corresponding to the actively shielded magnet 7A shown in FIG. 11(a). The active shielding reduces the distance that the 5 Gauss line extends from the centre of the actively shielded magnet 7A from about 4 m to about 1 m in the +Z direction and 2.5 m in the −Z direction when compared to the unshielded magnet 7 of FIG. 10. The active shielding reduces the distance that the 5 Gauss line extends from the centre of the actively shielded magnet 7A from about 3 m to about 2 m in the Y direction when compared to the unshielded magnet 7 of FIG. 10.

Figure 11C:
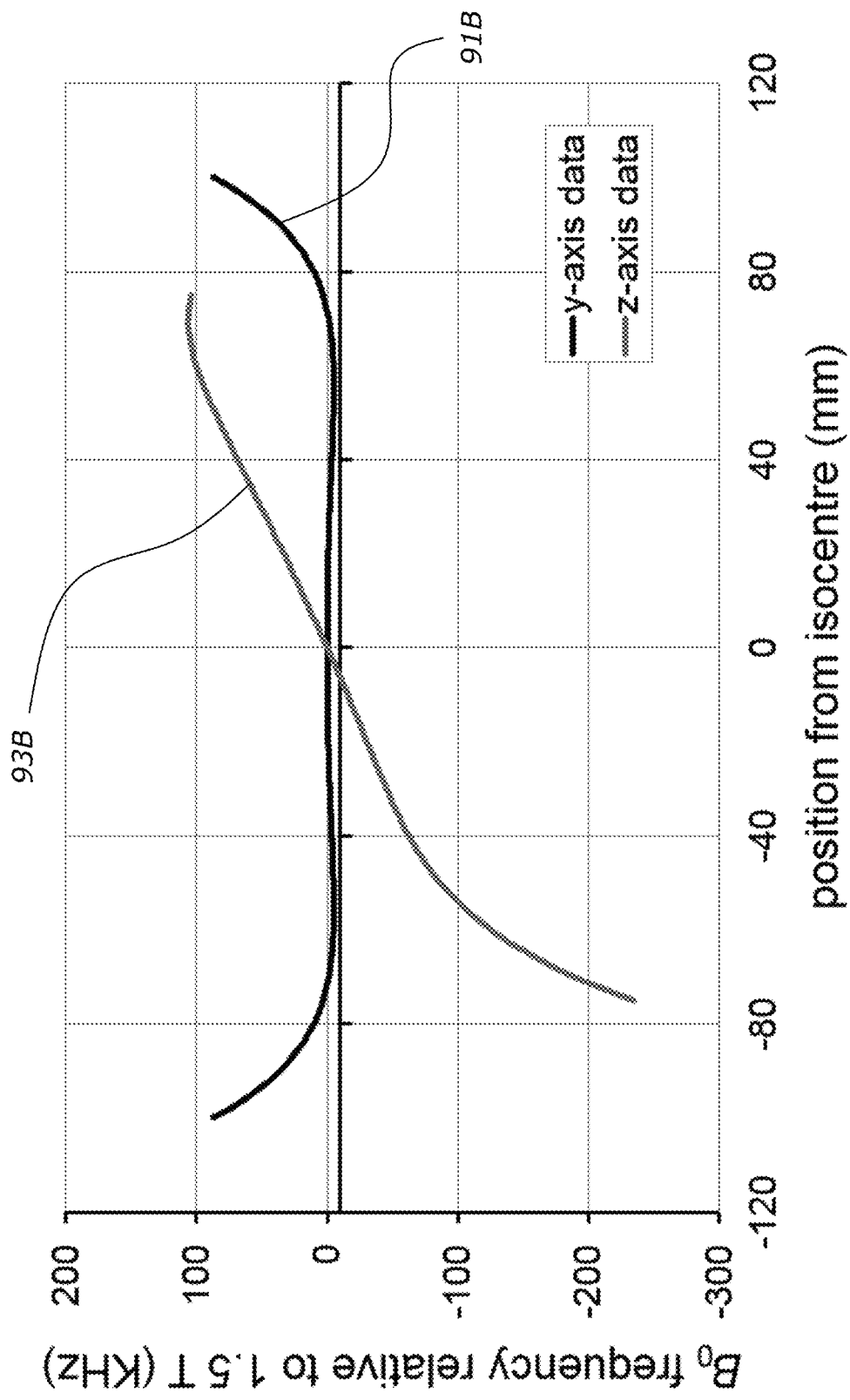
FIG. 11(c) is a graph of the magnetic field variation across the imaging volume for the actively shielded magnet.

FIG. 11(c) shows the magnetic field variation across the imaging volume for the actively shielded magnet 7A. Plot 91B shows the magnetic field variation in the Y direction (forward-to-rearward). Plot 93B shows the magnetic field variation in the Z direction (bottom-to-top). At least a major part of the imaging volume in the forward-to-rearward direction has a substantially zero magnetic field gradient 91B in a radial direction. At least a major part of the imaging volume in the bottom-to-top direction has a substantially linear non-zero magnetic field gradient 93B along the Z (cylindrical) axis. This is consistent with the magnetic field variation for the unshielded magnet 7 shown in FIG. 10(c).

Alternatively, in an embodiment, the MRI apparatus 1 comprises passive magnetic shielding. The passive shielding may be formed from a steel yoke that surrounds the outside of the magnet 7 to act as a return path for the magnetic flux generated by the magnet 7.

The above description is concerned primarily with the magnet and associated components. It will be understood by those skilled in the art that suitable gradient and radio-frequency coils will also be used with the magnet and associated components to achieve MRI.

Providing of Image—Pulse Sequences

Conventionally, an ultra-short magnet such as the magnet 7 would require an excessive amount of conductor to meet MRI homogeneity requirements (typical limit of around 2 ppm of field variation). However, with use of pulse sequences such as those described in PCT International Patent Application No. PCT/US2017/056487 (Systems and Methods for Steady-State Echo Magnetic Resonance Imaging), high quality images can be produced with up to around 3000 ppm of field variation within the imaging volume. Magnet 7 is within acceptable limits for use with both the MP-SSFP and STEREO pulse sequences, both of which have been shown to work in the presence of field variation exceeding 3000 ppm.

Figure 12:
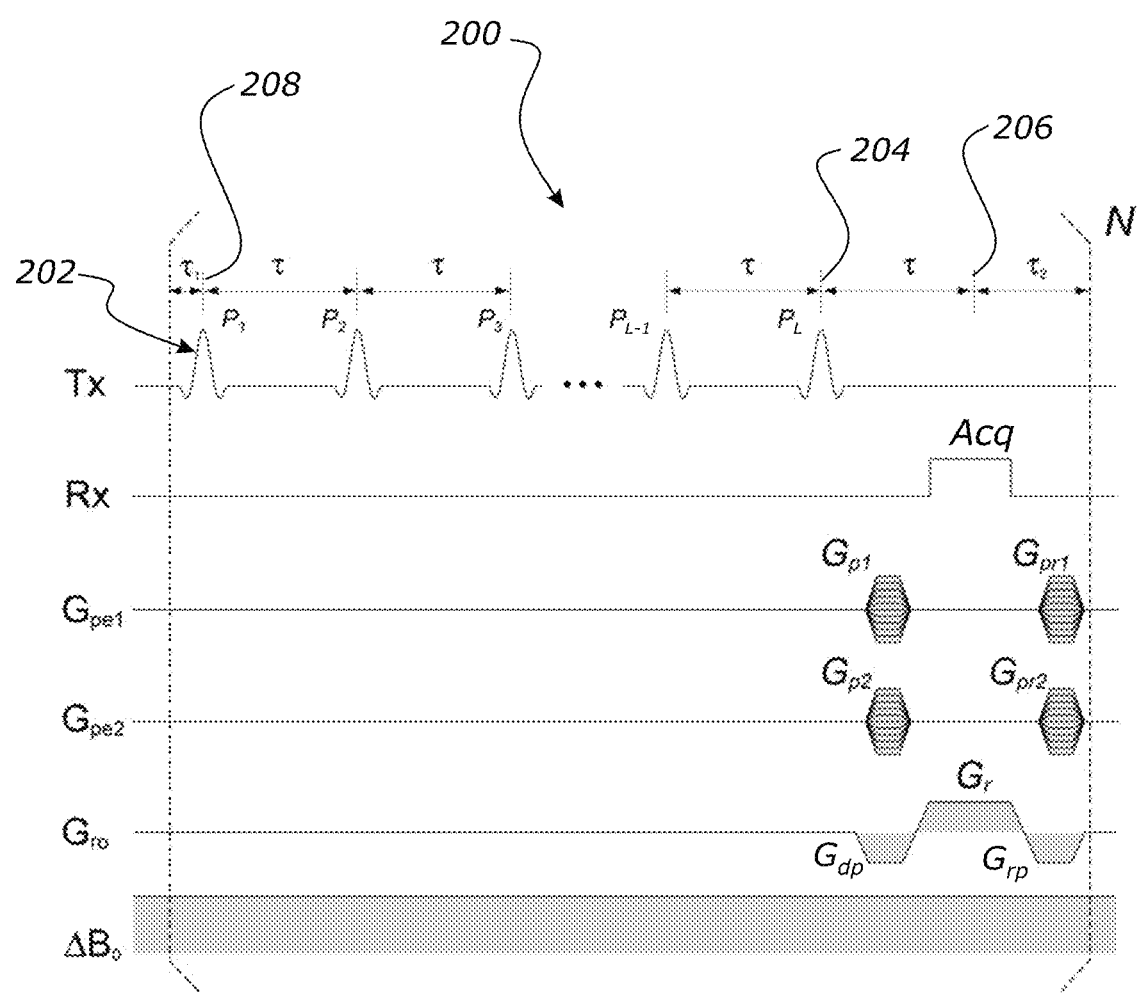
FIG. 12 is a schematic diagram of an exemplary pulse sequence that can be used with the magnet.

Referring to FIG. 12, one non-limiting example of a pulse sequence that can be used with the magnet 7 is shown. In the illustrated pulse sequence 200, spin magnetization can be excited with an RF pulse train 202 under a spatially inhomogeneous magnetic field $\Delta B_0$. In the RF pulse train 202, L individual RF excitation pulses ($P_j$; j=1, 2, ... L) are applied with a constant time interval, $\tau$. The waveform of the RF pulses ($P_j$; j=1, 2, ... L) in the RF pulse train 202 can be an amplitude modulated pulse (e.g., hard pulse, sinc pulse, Gaussian pulse) or a frequency-modulated pulse (e.g., Chirp pulse, hyperbolic secant pulse). Each of the RF pulses ($P_j$; j=1, 2, ... L) in the RF pulse train 202 may have a common waveform and pulse duration (pw), but the flip angle ($a_j$) and phase ($p_j$) can be set arbitrarily. The excitation bandwidth (BW) of the RF pulses ($P_j$; j=1, 2, ... L) depend on the bandwidth of each pulse ($P_j$; j=1, 2, ... L) in the RF pulse train 202. After the RF pulse train 202, signal acquisition (Acq) is carried out following pulsed phase encoding gradients ($G_{p1}$ and $G_{p2}$).

An RF pulse train 202 of frequency swept RF pulses with relatively small flip angles (FA) can be used. In general, flip angles between 0 degrees to 179 degrees can be used. As one non-limiting example, flip angles between 0.5 degrees and 15 degrees can be used.

During signal acquisition (Acq), a pulsed readout gradient field ($G_r$) along with dephasing ($G_{dp}$) and rephasing ($G_{rp}$) gradients before and after the readout gradient ($G_r$) can be optionally applied. For example, the inhomogeneous magnetic field ($B_0$) can be partly compensated for with a pulsed readout gradient ($G_r$). Time between the center 204 of the last RF pulse ($P_L$) in the RF pulse train 202 and the center 206 of the signal acquisition window (Acq) is the same as the pulse interval ($\tau$) in the RF pulse train 202.

Following the signal acquisition, phase encode rephasing gradients ($G_{pr1}$, and $G_{pr2}$) are applied to rewind the spin phase introduced by the phase encoding gradients ($G_{p1}$ and $G_{p2}$). That is, the phase encode rephasing gradients ($G_{pr1}$, and $G_{pr2}$) serve the function of a rewinder applied with reverse polarity to ensure stability of the phase of the MR signal in each repetition.

The time between the center 206 of the acquisition window (Acq) and the center 208 of the first RF pulse ($P_1$) in the RF pulse train 202 is equal to the pulse interval ($\tau$) in the RF pulse train 202 (i.e., $\tau_1 + T_2 = \tau$). Therefore, the pulse sequence 200 includes an RF pulse train 202 composed of L+1 RF pulses with a constant interval ($\tau$), where the L+1th pulse can be replaced with data acquisition. Multiple echo acquisition can be conducted by replacing more than one RF pulse with data acquisitions, along with phase encoding and rewinding gradients. Either way, the radio-frequency magnetic field ($B_1$) produced by the RF pulse train 202 is consistent and is sufficient to overcome inconsistencies and inhomogeneities in the $B_0$ field. Generally, L has a value of at least 2, such that echoes refocus at the center of the acquisition window.

The pulse sequence 200 can be repeated N times to acquire refocusing echo signals Si (i=1, 2, ..., N) sufficient for 3D image reconstruction by changing the phase encoding gradients ($G_{p1}$ and $G_{p2}$) in successive repetitions. For example, when the phase encoding gradients ($G_{p1}$ and $G_{p2}$) are mutually orthogonal linear gradients in space and applied with constant increments, the number of repetitions, N, is represented by $N=N_{pe1} \times N_{pe2}$, in which $N_{pe1}$ and $N_{pe2}$ are the number of phase encoding steps along the two phase encoding directions. The pulsed readout gradient ($G_r$) and the phase encoding gradients ($G_{p1}$ and $G_{p2}$) can be spatially nonlinear gradients. The increments of phase encoding gradients can be arbitrary.

Other exemplary pulse sequences that can be used include those described in U.S. patent application Ser. No. 13/743,902 (Steering Resonance Along a Trajectory) and U.S. patent application Ser. No. 14/174,368 (Beam Steering With Resonance Along a Trajectory).

All of the above patent applications are incorporated herein in their entirety by way of reference.

Use of the Apparatus

In use of the apparatus 1, the patient P will be positioned in the apparatus 1 so that their head is positioned in the magnet 7 with the centre of their brain aligned with the isocentre 37 and their eyes facing the window 9 so they can see outside the apparatus 1.

The apparatus 1 is then operated to provide MRI images of the patient's brain, via the application of suitable pulse sequences. The images of the patient's brain will be output to a suitable interface such as a display device, storage device, or printer.

The medical provider can interact with the patent visually via the window, or tactilely via the patient's arms or hands which are exposed from the magnet. This also enables the patient to manipulate objects outside the magnet while the brain is imaged.

Providing visual stimulation to the patient enables the brain to be imaged during the visual stimulation, making the apparatus particularly suitable for neural imaging.

A head only MRI apparatus 1 that uses a pulse sequence as described above in combination with the compact magnet 7 may overcome many of the disadvantages of known MRI apparatuses. For example, the ability to tolerate high field variation enables the MRI apparatus 1 to have a window 9. The window 9 may reduce the feeling of claustrophobia in patients because it enables a patient to see out of the apparatus 1. The window 9 may also improve communication between a medical provider and a patient because it enables the medical provider to provide visual cues to the patient.

The compact size of the magnet 7 means that the apparatus 1 does not receive the patient's shoulders. Therefore, the patient may retain full use of their arms when their head is received by the apparatus 1.

The compact size of the magnet 7 also enables the apparatus 1 to be more easily transported or moved than conventional MRI apparatuses. The coils also require significantly less superconducting material than conventional MRI apparatuses, so HTS material, which is typically significantly more expensive than LTS material, is a viable option for the superconducting material. If HTS material is used, a cryocooler may be used instead of the cryogen bath typically required for LTS MRI machines, further improving the transportability of the apparatus 1.

The above describes exemplary embodiments of the present invention, and modifications may be made thereto without departing from the scope of the present invention.

For example, where particular configurations, dimensions, and numbers of components are shown, these are exemplary and may be varied without departing from the scope of the present invention.

The invention claimed is:

1. A magnet for use in an apparatus for performing magnetic resonance imaging (MRI) of a patient's head, wherein the magnet is an asymmetric magnet comprising:
   a plurality of coils that are aligned along a cylindrical axis to provide a magnetic field on the cylindrical axis;
   a patient end arranged to be positioned adjacent or against a patient's shoulders with the patient's shoulders outside the magnet; and
   a recess for receipt of the patient's head and extending into the magnet from the patient end,
   wherein the magnet is configured to provide an imaging volume that is positioned along the cylindrical axis of the magnet in the recess, and wherein at least a major part of the imaging volume has a substantially linear non-zero magnetic field gradient along the cylindrical axis.

2. The magnet according to claim 1, wherein at least about 75% of the imaging volume has a substantially linear magnetic field gradient along the cylindrical axis.

3. The magnet according to claim 1, wherein the magnetic field generally increases in a direction from the patient end to an opposite end of the magnet, along the cylindrical axis.

4. The magnet according to claim 1, wherein the magnetic field generally decreases in a direction from the patient end to an opposite end of the magnet, along the cylindrical axis.

5. The magnet according to claim 1, wherein the imaging volume is positioned closer to the patient end of the magnet than to an opposite end of the magnet, along the cylindrical axis.

6. The magnet according to claim 1, wherein the magnet comprises a plurality of superconducting coils.

7. The magnet according to claim 1, wherein the magnet comprises at least three groups of coils, with at least one group of coils positioned at or toward the patient end having a larger transverse outer dimension than at least one group of coils positioned at or toward the opposite end of the magnet.

8. The magnet according to claim 1, wherein the magnet comprises a first group of coils positioned at or toward the patient end and having a first relatively large transverse outer dimension, a second group of coils positioned further from the patient end and having a second relatively small transverse outer dimension, and a third group of coils positioned at or toward the opposite end and having a third transverse outer dimension that is smaller than the second transverse outer dimension.

9. The magnet according to claim 8, wherein the first, second, and third groups of coils are arranged to provide a summation of magnetic field from the first, second, and third group of coils and provide a magnetic field in a first sense.

10. The magnet according to claim 9, wherein the first, second, and third groups of coils have the same winding direction.

11. The magnet according to claim 9, wherein the magnet comprises at least one additional group of coils that is arranged to provide a magnetic field in a second sense that is opposite to the first sense.

12. The magnet according to claim 11, wherein the at least one additional group of coils has a winding direction opposite to the first, second, and third groups of coils.

13. The magnet according to claim 11, wherein the at least one additional group of coils is operatively connected to receive current in an opposite sense to the current that is received by the first, second, and third groups of coils.

14. The magnet according to claim 11, wherein said at least one additional group of coils consists of one group of coils, and said one group of coils is positioned between the first group of coils and the second group of coils.

15. The magnet according to claim 14, wherein said one group of coils has a transverse outer dimension that is smaller than the transverse outer dimension of the first group of coils and the transverse outer dimension of the second group of coils.

16. A magnet for use in an apparatus for performing magnetic resonance imaging (MRI) of a patient's head, wherein the magnet is an asymmetric magnet comprising a plurality of superconducting coils that are positioned around a cylindrical axis to provide a magnetic field on the cylindrical axis, wherein the magnet comprises:
   a patient end arranged to be positioned adjacent or against a patient's shoulders with the patient's shoulders outside the magnet; and
   a recess for receipt of the patient's head extending into the magnet from the patient end,
   wherein the magnet is configured to provide an offset imaging volume in the recess, wherein the imaging volume has an isocentre that is positioned closer to the patient end of the magnet than to the opposite end of the magnet; and
   wherein the magnet comprises at least three groups of coils in a generally tapering arrangement, with a first group of coils positioned at or toward the patient end having a larger transverse outer dimension than a transverse outer dimension of a second group of coils positioned further from the patient end, and a third group of coils positioned at or toward an opposite end of the magnet having a transverse outer dimension that is smaller than the transverse outer dimension of the second group of coils.

17. The magnet according to claim 16, wherein the magnet is configured to only receive the patient's head and optionally part of the patient's neck, such that the magnet is configured for use as part of a head-only MRI apparatus.

18. The magnet according to claim 16, wherein the magnet defines the cylindrical axis, and the recess and the imaging volume are coaxial with the cylindrical axis.

19. The magnet according to claim 16, wherein the isocentre is positioned between about 120 mm and about 170 mm from the patient end of the magnet, optionally between about 75 mm and about 165 mm above a patient end of the first group of coils, optionally between about 189 mm and about 200 mm below a top of the third group of coils, and optionally wherein the magnet has a length from the patient end to the opposite end of between about 350 mm and about 400 mm.

20. The magnet according to claim 16, wherein the imaging volume has a substantially ellipsoidal shape.

* * * * *